(12) United States Patent
Chappa et al.

(10) Patent No.: US 11,090,468 B2
(45) Date of Patent: Aug. 17, 2021

(54) APPARATUS AND METHODS FOR COATING MEDICAL DEVICES

(71) Applicant: SurModics, Inc., Eden Prairie, MN (US)

(72) Inventors: Ralph A. Chappa, Ham Lake, MN (US); Mark F. Carlson, St. Louis Park, MN (US)

(73) Assignee: Surmodics, Inc., Eden Prairie, MN (US)

( * ) Notice: Subject to any disclaimer, the term of this patent is extended or adjusted under 35 U.S.C. 154(b) by 308 days.

(21) Appl. No.: 14/063,113

(22) Filed: Oct. 25, 2013

(65) Prior Publication Data

US 2014/0121597 A1 May 1, 2014

Related U.S. Application Data

(60) Provisional application No. 61/718,358, filed on Oct. 25, 2012.

(51) Int. Cl.
*A61M 25/10* (2013.01)
*A61M 25/00* (2006.01)
(Continued)

(52) U.S. Cl.
CPC .... *A61M 25/1029* (2013.01); *A61M 25/0009* (2013.01); *B05B 13/0228* (2013.01);
(Continued)

(58) Field of Classification Search
CPC ........... A61L 2420/02; A61L 2300/606; B05B 13/0228; B05B 13/0235; B05B 13/0405;
(Continued)

(56) References Cited

U.S. PATENT DOCUMENTS

| 554,114 A | 2/1896 | Evertz |
| 1,281,672 A | 10/1918 | Schorn |

(Continued)

FOREIGN PATENT DOCUMENTS

| CA | 2351016 | 12/2001 |
| DE | 3335502 | 9/1983 |

(Continued)

OTHER PUBLICATIONS

"Communication Pursuant to Rules 161(1) and 162 EPC," for European Patent Application No. 14730319.2, dated Dec. 22, 2015 (2 pages).

(Continued)

*Primary Examiner* — Scott J Medway
(74) *Attorney, Agent, or Firm* — Pauly, DeVries Smith & Deffner LLC

(57) ABSTRACT

Embodiments of the invention include apparatus and methods for coating medical devices. In an embodiment, the invention includes a coating apparatus including a coating application unit including a fluid applicator; a first rotation mechanism and a second rotation mechanism; and a controller, wherein the controller causes the first rotation mechanism and the second rotation mechanism to rotate a medical device at substantially the same speed, wherein the speed is greater than 500 rotations per minute. In an embodiment, the invention includes a method of coating a medical device including rotating a medical device with a rotation mechanism at a speed of greater than 500 rotations per minute; contacting the medical device with a fluid applicator; and applying a coating solution to the device. In an embodiment, the invention includes a medical device. In some embodiments a surface of a shaft of the device comprises high points and low points.

17 Claims, 8 Drawing Sheets

(51) Int. Cl.
*B05D 1/00* (2006.01)
*B05B 13/02* (2006.01)

(52) U.S. Cl.
CPC .......... *B05D 1/002* (2013.01); *A61L 2400/10* (2013.01); *A61L 2420/02* (2013.01); *A61M 25/0045* (2013.01); *A61M 2025/1031* (2013.01)

(58) Field of Classification Search
CPC ..... B05B 5/082; B05B 13/0431; B05D 1/002; B05D 1/02; B05D 1/26; A61M 25/104; A61M 2025/1031; A61M 2025/0056; A61M 25/1029; A61M 25/0045; A45D 34/04; A45D 40/26; A45D 40/261; A45D 34/00; A61C 19/066; A61C 17/227; A61C 19/063; B05C 1/06; B05C 17/0357; B05C 17/0217; B05C 17/0341; B05C 17/0308
See application file for complete search history.

(56) References Cited

U.S. PATENT DOCUMENTS

| | | | |
|---|---|---|---|
| 1,866,100 A | 7/1932 | Hach | |
| 2,329,438 A * | 9/1943 | Fiedler, Jr. | E04F 21/32 425/183 |
| 2,330,880 A | 10/1943 | Gladfelter et al. | |
| 2,335,116 A | 11/1943 | Hansen | |
| 2,398,506 A * | 4/1946 | Rogers | G02B 5/3033 359/487.05 |
| 2,493,787 A | 1/1950 | Torretti | |
| 2,781,280 A | 2/1957 | Miller | |
| 2,821,158 A | 1/1958 | Brown et al. | |
| 2,881,461 A * | 4/1959 | Parker | B05C 17/0227 15/230.11 |
| 3,198,170 A | 8/1965 | Toshio | |
| 3,318,281 A | 5/1967 | Plegat | |
| 3,348,954 A * | 10/1967 | Good | B05C 3/18 118/401 |
| 3,466,131 A * | 9/1969 | Arcudi | B65D 83/00 401/132 |
| 3,502,494 A * | 3/1970 | Yosuke | B05C 5/0254 118/411 |
| 3,645,773 A * | 2/1972 | Herzhoff | B05D 1/26 118/410 |
| 3,663,292 A * | 5/1972 | Herzhoff | B05C 5/0254 118/410 |
| 3,699,917 A | 10/1972 | Deverse et al. | |
| 3,702,739 A * | 11/1972 | Rentfrow | A45D 34/041 401/197 |
| 3,723,120 A | 3/1973 | Hummel et al. | |
| 3,736,199 A * | 5/1973 | Mason | B60R 13/04 156/71 |
| 3,837,805 A | 9/1974 | Boucher | |
| 3,935,896 A | 2/1976 | Tegtmeier et al. | |
| 3,936,549 A | 2/1976 | Kohler et al. | |
| 3,963,069 A | 6/1976 | Marti et al. | |
| 3,966,120 A | 6/1976 | Furgalus et al. | |
| 4,000,745 A | 1/1977 | Goldberg | |
| 4,016,306 A | 4/1977 | Miyagawa et al. | |
| 4,051,805 A | 10/1977 | Waldrum | |
| 4,060,116 A | 11/1977 | Frailly | |
| 4,073,335 A | 2/1978 | Fort et al. | |
| 4,075,975 A | 2/1978 | Oswald | |
| 4,082,870 A | 4/1978 | Yenni | |
| 4,146,036 A | 3/1979 | Dutcher et al. | |
| 4,148,934 A | 4/1979 | Baker | |
| 4,153,201 A | 5/1979 | Berger et al. | |
| 4,174,678 A | 11/1979 | Van Den Bergh | |
| 4,195,637 A | 4/1980 | Gruntzig et al. | |
| 4,196,231 A | 4/1980 | Hubers | |
| 4,197,338 A * | 4/1980 | Perna | B05C 17/0212 15/230.11 |
| 4,206,756 A | 6/1980 | Grossan | |
| 4,209,019 A | 6/1980 | Dutcher et al. | |
| 4,240,373 A | 12/1980 | Anger | |
| 4,257,343 A * | 3/1981 | Kullander | B05C 3/18 118/126 |
| 4,289,089 A | 9/1981 | Tacke et al. | |
| 4,300,557 A | 11/1981 | Refojo et al. | |
| 4,301,968 A | 11/1981 | Berger et al. | |
| 4,337,896 A | 7/1982 | Berger et al. | |
| 4,352,459 A | 10/1982 | Berger et al. | |
| 4,364,879 A | 12/1982 | Gut et al. | |
| 4,375,820 A | 3/1983 | Vinarcsik et al. | |
| 4,415,654 A | 11/1983 | Pohl | |
| 4,475,972 A * | 10/1984 | Wong | 156/167 |
| 4,503,802 A | 3/1985 | Keller et al. | |
| 4,541,564 A | 9/1985 | Berger et al. | |
| 4,544,626 A | 10/1985 | Sullivan | |
| 4,567,934 A | 2/1986 | Nakao et al. | |
| 4,572,451 A | 2/1986 | Ikeda et al. | |
| 4,575,330 A | 3/1986 | Hull | |
| 4,603,058 A | 7/1986 | Adams | |
| 4,616,593 A | 10/1986 | Kawamura et al. | |
| 4,622,917 A | 11/1986 | Schramm | |
| 4,638,045 A | 1/1987 | Kohn et al. | |
| 4,655,393 A | 4/1987 | Berger | |
| 4,678,466 A | 7/1987 | Rosenwald | |
| 4,723,708 A | 2/1988 | Berger et al. | |
| 4,743,252 A | 5/1988 | Martin, Jr. et al. | |
| 4,767,229 A * | 8/1988 | Cha | B05C 17/02 401/208 |
| 4,819,661 A | 4/1989 | Heil et al. | |
| 4,824,017 A | 4/1989 | Mansfield | |
| 4,927,741 A | 5/1990 | Garth et al. | |
| 4,953,564 A | 9/1990 | Berthlelsen | |
| 4,971,895 A | 11/1990 | Sullivan | |
| 4,972,848 A | 11/1990 | Di Domenico et al. | |
| 4,978,067 A | 12/1990 | Berger et al. | |
| 4,988,883 A | 1/1991 | Oppawsky | |
| 5,002,067 A | 3/1991 | Berthelsen et al. | |
| 5,002,582 A | 3/1991 | Guire et al. | |
| 5,003,992 A | 4/1991 | Holleman et al. | |
| 5,036,634 A | 8/1991 | Lessard et al. | |
| 5,041,089 A | 8/1991 | Mueller et al. | |
| 5,049,404 A | 9/1991 | Kisler et al. | |
| 5,069,940 A | 12/1991 | Wenrick | |
| 5,071,337 A | 12/1991 | Heller et al. | |
| 5,076,285 A | 12/1991 | Hess et al. | |
| 5,076,974 A | 12/1991 | Modrek et al. | |
| 5,087,246 A | 2/1992 | Smith | |
| 5,090,084 A * | 2/1992 | De Guzman | A47L 13/11 15/230.11 |
| 5,102,402 A | 4/1992 | Dror et al. | |
| 5,120,312 A | 6/1992 | Wigness et al. | |
| 5,164,188 A | 11/1992 | Wong | |
| 5,183,509 A | 2/1993 | Brown et al. | |
| 5,207,343 A | 5/1993 | Bogadi | |
| 5,219,120 A | 6/1993 | Ehrenberg et al. | |
| 5,219,690 A * | 6/1993 | Hammond | 430/58.05 |
| 5,248,752 A | 9/1993 | Argyropoulos et al. | |
| 5,254,164 A | 10/1993 | Masahumi | |
| 5,255,693 A | 10/1993 | Dutcher et al. | |
| 5,300,108 A | 4/1994 | Rebell et al. | |
| 5,300,114 A | 4/1994 | Gwon | |
| 5,304,121 A | 4/1994 | Sahatjian | |
| 5,318,587 A | 6/1994 | Davey | |
| 5,324,325 A | 6/1994 | Moaddeb | |
| 5,344,298 A | 9/1994 | Hull | |
| 5,364,343 A | 11/1994 | Apolet et al. | |
| 5,372,577 A | 12/1994 | Ungerleider | |
| 5,378,475 A | 1/1995 | Smith et al. | |
| 5,382,234 A | 1/1995 | Cornelius et al. | |
| 5,385,148 A | 1/1995 | Lesh et al. | |
| 5,387,247 A | 2/1995 | Vallana et al. | |
| 5,405,376 A | 4/1995 | Mulier et al. | |
| 5,405,631 A | 4/1995 | Rosenthal | |
| 5,410,773 A * | 5/1995 | Forkner | B05C 17/0212 15/145 |
| 5,413,638 A | 5/1995 | Bernstein, Jr. et al. | |
| 5,414,075 A | 5/1995 | Swan et al. | |
| 5,421,979 A | 6/1995 | Stevenson | |

(56) References Cited

U.S. PATENT DOCUMENTS

| | | | |
|---|---|---|---|
| 5,431,649 | A | 7/1995 | Mulier et al. |
| 5,466,233 | A | 11/1995 | Weiner et al. |
| 5,472,436 | A | 12/1995 | Fremstad |
| 5,476,511 | A | 12/1995 | Gwon et al. |
| 5,501,735 | A | 3/1996 | Pender |
| 5,527,389 | A | 6/1996 | Rosenblum et al. |
| 5,538,353 | A * | 7/1996 | DeHavilland .......... A45D 34/04 401/132 |
| 5,571,089 | A | 11/1996 | Crocker |
| 5,582,616 | A | 12/1996 | Bolduc et al. |
| 5,618,568 | A * | 4/1997 | Krupa ................ B29C 47/0021 264/101 |
| 5,626,919 | A | 5/1997 | Chapman et al. |
| 5,630,879 | A | 5/1997 | Eichmann et al. |
| 5,637,460 | A | 6/1997 | Swan et al. |
| 5,643,362 | A | 7/1997 | Garves |
| 5,645,592 | A | 7/1997 | Nicolais et al. |
| 5,656,332 | A | 8/1997 | Saito et al. |
| 5,658,387 | A | 8/1997 | Reardon et al. |
| 5,673,473 | A | 10/1997 | Johnson et al. |
| 5,679,400 | A | 10/1997 | Tuch |
| 5,714,360 | A | 2/1998 | Swan et al. |
| 5,716,151 | A * | 2/1998 | Satake ................ A45D 34/041 401/187 |
| 5,743,964 | A | 4/1998 | Pankake |
| 5,776,101 | A | 7/1998 | Goy |
| 5,788,772 | A | 8/1998 | Kunieda et al. |
| 5,807,331 | A | 9/1998 | Den Heijer et al. |
| 5,807,395 | A | 9/1998 | Mulier et al. |
| 5,810,836 | A | 9/1998 | Hussein et al. |
| 5,833,715 | A | 11/1998 | Vachon et al. |
| 5,833,891 | A | 11/1998 | Subramaniam et al. |
| 5,837,008 | A | 11/1998 | Berg et al. |
| 5,837,088 | A | 11/1998 | Palmgren et al. |
| 5,849,359 | A | 12/1998 | Burns et al. |
| 5,858,435 | A | 1/1999 | Gallo |
| 5,868,697 | A | 2/1999 | Richter et al. |
| 5,882,336 | A | 3/1999 | Janacek |
| 5,882,405 | A | 3/1999 | Kish et al. |
| 5,897,911 | A | 4/1999 | Loeffler |
| 5,904,144 | A | 5/1999 | Hammang et al. |
| 5,913,653 | A | 6/1999 | Kempf |
| 5,921,982 | A | 7/1999 | Lesh et al. |
| 5,925,885 | A | 7/1999 | Clark et al. |
| 5,928,662 | A | 7/1999 | Phillips |
| 5,972,027 | A | 10/1999 | Johnson |
| 5,972,369 | A | 10/1999 | Roorda et al. |
| 5,976,256 | A | 11/1999 | Kawano |
| 5,992,568 | A * | 11/1999 | Craig ...................... B61K 3/02 105/72.2 |
| 6,001,425 | A | 12/1999 | Stash et al. |
| 6,019,784 | A | 2/2000 | Hines |
| 6,033,582 | A | 3/2000 | Lee et al. |
| 6,053,924 | A | 4/2000 | Hussein |
| 6,056,998 | A | 5/2000 | Fujimoto |
| 6,070,697 | A * | 6/2000 | Millard ...................... F16N 7/12 184/15.1 |
| 6,074,661 | A | 6/2000 | Olejnik et al. |
| 6,091,978 | A | 7/2000 | Johnson et al. |
| 6,094,887 | A | 8/2000 | Swank et al. |
| 6,102,887 | A | 8/2000 | Altman |
| 6,117,456 | A | 9/2000 | Lee et al. |
| 6,153,252 | A | 11/2000 | Hossainy et al. |
| 6,156,373 | A | 12/2000 | Zhong et al. |
| 6,156,526 | A | 12/2000 | Newman |
| 6,190,077 | B1 * | 2/2001 | Newson ............... A01M 21/043 401/192 |
| 6,197,324 | B1 | 3/2001 | Crittenden |
| 6,203,551 | B1 | 3/2001 | Wu |
| 6,203,556 | B1 | 3/2001 | Evans et al. |
| 6,203,732 | B1 | 3/2001 | Clubb et al. |
| 6,207,337 | B1 | 3/2001 | Swain |
| 6,212,434 | B1 | 4/2001 | Scheiner et al. |
| 6,214,008 | B1 | 4/2001 | Illi |
| 6,214,115 | B1 | 4/2001 | Taylor et al. |
| 6,218,016 | B1 | 4/2001 | Tedeschi |
| 6,245,089 | B1 | 6/2001 | Daniel et al. |
| 6,245,099 | B1 | 6/2001 | Edwin et al. |
| 6,248,112 | B1 | 6/2001 | Gambale et al. |
| 6,251,090 | B1 | 6/2001 | Avery et al. |
| 6,251,418 | B1 | 6/2001 | Ahern et al. |
| 6,254,921 | B1 | 7/2001 | Chappa et al. |
| 6,278,018 | B1 | 8/2001 | Swan |
| 6,279,505 | B1 | 8/2001 | Plester et al. |
| 6,290,728 | B1 | 9/2001 | Phelps et al. |
| 6,298,272 | B1 | 10/2001 | Peterfeso et al. |
| 6,303,148 | B1 | 10/2001 | Hennink et al. |
| 6,306,125 | B1 | 10/2001 | Parker et al. |
| 6,309,370 | B1 | 10/2001 | Haim et al. |
| 6,322,847 | B1 | 11/2001 | Zhong et al. |
| 6,333,595 | B1 | 12/2001 | Horikawa et al. |
| 6,345,630 | B2 | 2/2002 | Fishkin et al. |
| 6,358,247 | B1 | 3/2002 | Altman et al. |
| 6,358,556 | B1 | 3/2002 | Ding et al. |
| 6,360,129 | B1 | 3/2002 | Ley et al. |
| 6,368,658 | B1 | 4/2002 | Schwarz et al. |
| 6,394,995 | B1 | 5/2002 | Solar et al. |
| 6,395,326 | B1 | 5/2002 | Castro et al. |
| 6,406,754 | B2 | 6/2002 | Chappa et al. |
| 6,431,770 | B1 | 8/2002 | Kurematsu et al. |
| 6,435,959 | B1 | 8/2002 | Skrmetta |
| 6,478,776 | B1 | 11/2002 | Rosenman et al. |
| 6,501,994 | B1 | 12/2002 | Janke et al. |
| 6,505,082 | B1 | 1/2003 | Scheiner et al. |
| 6,506,437 | B1 | 1/2003 | Harish et al. |
| 6,517,515 | B1 | 2/2003 | Eidenschink |
| 6,517,889 | B1 | 2/2003 | Jayaraman |
| 6,521,299 | B1 | 2/2003 | Dessauer |
| 6,527,863 | B1 | 3/2003 | Pacetti et al. |
| 6,544,582 | B1 | 4/2003 | Yoe |
| 6,547,787 | B1 | 4/2003 | Altman et al. |
| 6,555,157 | B1 | 4/2003 | Hossainy |
| 6,562,051 | B1 | 5/2003 | Bolduc et al. |
| 6,562,136 | B1 | 5/2003 | Chappa et al. |
| 6,565,659 | B1 | 5/2003 | Pacetti et al. |
| 6,572,644 | B1 | 6/2003 | Moein |
| 6,595,958 | B1 | 7/2003 | Mickley |
| 6,599,560 | B1 | 7/2003 | Daggett et al. |
| 6,605,154 | B1 | 8/2003 | Villareal |
| 6,607,598 | B2 | 8/2003 | Schwarz et al. |
| 6,613,017 | B1 | 9/2003 | Mickley |
| 6,616,765 | B1 | 9/2003 | Castro et al. |
| 6,623,504 | B2 | 9/2003 | Vrba et al. |
| 6,656,529 | B1 | 12/2003 | Pankake |
| 6,669,980 | B2 | 12/2003 | Hansen |
| 6,669,994 | B2 | 12/2003 | Swan et al. |
| 6,673,154 | B1 | 1/2004 | Pacetti et al. |
| 6,676,987 | B2 | 1/2004 | Zhong et al. |
| 6,695,920 | B1 | 2/2004 | Pacetti et al. |
| 6,706,023 | B1 | 3/2004 | Huttner et al. |
| 6,709,514 | B1 | 3/2004 | Hossainy |
| 6,709,712 | B2 | 3/2004 | Chappa et al. |
| 6,716,081 | B2 | 4/2004 | Kim et al. |
| 6,716,196 | B2 | 4/2004 | Lesh et al. |
| 6,719,750 | B2 | 4/2004 | Varner et al. |
| 6,719,805 | B1 | 4/2004 | Ahern |
| 6,723,373 | B1 | 4/2004 | Narayanan et al. |
| 6,725,901 | B1 | 4/2004 | Kramer et al. |
| 6,743,233 | B1 | 6/2004 | Baldwin et al. |
| 6,743,462 | B1 | 6/2004 | Pacetti |
| 6,743,463 | B2 | 6/2004 | Weber et al. |
| 6,752,959 | B2 | 6/2004 | Smith et al. |
| 6,764,470 | B2 | 7/2004 | Dimick |
| 6,783,793 | B1 | 8/2004 | Hossainy et al. |
| 6,803,070 | B2 | 10/2004 | Weber |
| 6,818,063 | B1 | 11/2004 | Kerrigan |
| 6,896,842 | B1 | 5/2005 | Hamilton et al. |
| 6,941,632 | B1 * | 9/2005 | Mead .................... B29C 70/342 156/349 |
| 6,981,982 | B2 | 1/2006 | Armstrong et al. |
| 7,010,933 | B2 | 3/2006 | Ishitomi et al. |
| 7,041,174 | B2 | 5/2006 | Carlson et al. |
| 7,045,015 | B2 | 5/2006 | Renn et al. |

(56) References Cited

U.S. PATENT DOCUMENTS

| | | | |
|---|---|---|---|
| 7,077,910 B2 | 7/2006 | Chappa et al. | |
| 7,087,658 B2 | 8/2006 | Swan et al. | |
| 7,090,421 B1* | 8/2006 | Mead | B05C 17/0232 15/230.11 |
| 7,105,350 B2 | 9/2006 | Foster et al. | |
| 7,125,577 B2 | 10/2006 | Chappa | |
| 7,163,523 B2 | 1/2007 | Devens, Jr. et al. | |
| 7,186,374 B2 | 3/2007 | Zelina et al. | |
| 7,192,484 B2 | 3/2007 | Chappa et al. | |
| 7,198,675 B2 | 4/2007 | Fox et al. | |
| 7,226,231 B2* | 6/2007 | Py | B65D 35/28 401/11 |
| 7,335,314 B2 | 2/2008 | Wu et al. | |
| 7,563,324 B1 | 7/2009 | Chen et al. | |
| 7,611,532 B2 | 11/2009 | Bates et al. | |
| 7,638,156 B1* | 12/2009 | Hossainy et al. | 427/2.1 |
| 7,669,548 B2 | 3/2010 | Chappa | |
| 7,743,727 B2 | 6/2010 | Shekalim | |
| 7,806,612 B1* | 10/2010 | Wangler | A46B 9/005 15/230.11 |
| 7,883,749 B2 | 2/2011 | Carlson | |
| 7,958,840 B2 | 6/2011 | Chappa | |
| 8,003,156 B2 | 8/2011 | Van Sciver | |
| 8,166,909 B2 | 5/2012 | Chappa | |
| 8,171,595 B1* | 5/2012 | Umhoefer, Jr. | B05C 17/0207 15/230.11 |
| 8,246,974 B2 | 8/2012 | Chappa | |
| 8,262,592 B1* | 9/2012 | Brooks | A61H 23/02 601/17 |
| 8,282,981 B2* | 10/2012 | Andreacchi | B05C 3/18 118/500 |
| 8,318,263 B2 | 11/2012 | Carlson et al. | |
| D676,975 S* | 2/2013 | Bickford | D24/211 |
| 8,632,837 B2 | 1/2014 | Gong et al. | |
| 8,757,914 B1* | 6/2014 | Megaro | B05B 11/3052 401/219 |
| 2,253,019 A1 | 8/2014 | Crepeau | |
| 8,844,543 B2* | 9/2014 | Bickford | A45D 34/041 132/320 |
| 8,961,054 B2* | 2/2015 | Gilbert | A47J 37/0786 401/219 |
| 8,974,134 B2* | 3/2015 | Wilson | A45D 34/041 401/183 |
| 9,205,447 B2* | 12/2015 | Wilson | G02B 1/105 |
| 9,283,350 B2 | 3/2016 | Chappa et al. | |
| 9,308,355 B2 | 4/2016 | Chappa et al. | |
| 9,364,349 B2 | 6/2016 | Chappa et al. | |
| 9,623,215 B2 | 4/2017 | Chappa et al. | |
| 9,827,401 B2 | 11/2017 | Chappa et al. | |
| 9,975,141 B2* | 5/2018 | Johnston | B05C 17/0357 |
| 10,099,041 B2 | 10/2018 | Chappa et al. | |
| 10,507,309 B2 | 12/2019 | Chappa et al. | |
| 2001/0001824 A1 | 5/2001 | Wu | |
| 2002/0026176 A1 | 2/2002 | Varner et al. | |
| 2002/0046521 A1 | 4/2002 | Steinacker, Sr. et al. | |
| 2002/0051730 A1 | 5/2002 | Bodnar et al. | |
| 2002/0062730 A1 | 5/2002 | Thornton | |
| 2002/0082679 A1 | 6/2002 | Sirhan et al. | |
| 2002/0094440 A1 | 7/2002 | Llanos et al. | |
| 2002/0103526 A1 | 8/2002 | Steinke | |
| 2002/0107330 A1 | 8/2002 | Pinchuk et al. | |
| 2002/0115400 A1 | 8/2002 | Skrmetta | |
| 2002/0155212 A1 | 10/2002 | Hossainy | |
| 2002/0159915 A1 | 10/2002 | Zelina et al. | |
| 2002/0188037 A1 | 12/2002 | Chudzik et al. | |
| 2002/0188170 A1 | 12/2002 | Santamore et al. | |
| 2003/0003221 A1 | 1/2003 | Zhong et al. | |
| 2003/0014036 A1 | 1/2003 | Varner et al. | |
| 2003/0039689 A1 | 2/2003 | Chen et al. | |
| 2003/0044514 A1 | 3/2003 | Richard | |
| 2003/0054090 A1 | 3/2003 | Hansen | |
| 2003/0059520 A1 | 3/2003 | Chen et al. | |
| 2003/0059920 A1 | 3/2003 | Drohan et al. | |
| 2003/0060783 A1 | 3/2003 | Koole et al. | |
| 2003/0065332 A1 | 4/2003 | Tenhuisen et al. | |
| 2003/0088307 A1 | 5/2003 | Shulze et al. | |
| 2003/0113439 A1 | 6/2003 | Pacetti et al. | |
| 2003/0120200 A1 | 6/2003 | Bergheim et al. | |
| 2003/0143315 A1 | 7/2003 | Pui et al. | |
| 2003/0150380 A1 | 8/2003 | Yoe | |
| 2003/0152693 A1* | 8/2003 | Su | B05C 1/02 427/162 |
| 2003/0157241 A1 | 8/2003 | Hossainy et al. | |
| 2003/0181848 A1 | 9/2003 | Bergheim et al. | |
| 2003/0190420 A1 | 10/2003 | Chappa et al. | |
| 2003/0215564 A1* | 11/2003 | Heller et al. | 427/2.25 |
| 2003/0229333 A1 | 12/2003 | Ashton et al. | |
| 2004/0006146 A1 | 1/2004 | Evans et al. | |
| 2004/0034357 A1 | 2/2004 | Beane et al. | |
| 2004/0037886 A1 | 2/2004 | Hsu | |
| 2004/0062592 A1* | 4/2004 | Shekalim | A61L 31/10 401/208 |
| 2004/0062875 A1 | 4/2004 | Chappa et al. | |
| 2004/0073298 A1 | 4/2004 | Hossainy | |
| 2004/0081745 A1 | 4/2004 | Hansen | |
| 2004/0111818 A1* | 6/2004 | Ma | B05C 17/0212 15/230.11 |
| 2004/0133155 A1 | 7/2004 | Varner et al. | |
| 2004/0142013 A1 | 7/2004 | Rubsamen | |
| 2004/0143314 A1 | 7/2004 | Sommer et al. | |
| 2004/0161547 A1 | 8/2004 | Carlson et al. | |
| 2004/0185168 A1 | 9/2004 | Weber et al. | |
| 2004/0194704 A1 | 10/2004 | Chappa et al. | |
| 2004/0211362 A1 | 10/2004 | Castro et al. | |
| 2004/0213893 A1 | 10/2004 | Boulais | |
| 2005/0015142 A1* | 1/2005 | Austin | A61F 2/91 623/1.42 |
| 2005/0019371 A1 | 1/2005 | Anderson et al. | |
| 2005/0059956 A1 | 3/2005 | Varner et al. | |
| 2005/0098097 A1 | 5/2005 | Chen et al. | |
| 2005/0129732 A1 | 6/2005 | Rubsamen | |
| 2005/0142070 A1 | 6/2005 | Hartley | |
| 2005/0143363 A1 | 6/2005 | De Juan et al. | |
| 2005/0147690 A1 | 7/2005 | Masters et al. | |
| 2005/0158449 A1 | 7/2005 | Chappa | |
| 2005/0233061 A1* | 10/2005 | Schwarz | 427/2.1 |
| 2005/0233062 A1* | 10/2005 | Hossainy et al. | 427/2.1 |
| 2005/0240147 A1 | 10/2005 | Makower et al. | |
| 2005/0255142 A1 | 11/2005 | Chudzik et al. | |
| 2005/0271703 A1 | 12/2005 | Anderson et al. | |
| 2005/0271706 A1 | 12/2005 | Anderson et al. | |
| 2005/0276837 A1 | 12/2005 | Anderson et al. | |
| 2005/0281863 A1 | 12/2005 | Anderson et al. | |
| 2005/0287188 A1 | 12/2005 | Anderson et al. | |
| 2006/0020295 A1 | 1/2006 | Brockway et al. | |
| 2006/0029720 A1 | 2/2006 | Panos et al. | |
| 2006/0045981 A1 | 3/2006 | Tsushi et al. | |
| 2006/0064134 A1 | 3/2006 | Mazar et al. | |
| 2006/0064142 A1 | 3/2006 | Chavan et al. | |
| 2006/0074404 A1 | 4/2006 | Struble | |
| 2006/0088653 A1 | 4/2006 | Chappa | |
| 2006/0096535 A1 | 5/2006 | Haller et al. | |
| 2006/0110428 A1 | 5/2006 | De Juan et al. | |
| 2006/0111754 A1 | 5/2006 | Rezai et al. | |
| 2006/0116590 A1 | 6/2006 | Fayram et al. | |
| 2006/0165872 A1 | 7/2006 | Chappa et al. | |
| 2006/0191476 A1 | 8/2006 | Nagase et al. | |
| 2006/0269663 A1* | 11/2006 | Mori | 427/240 |
| 2007/0031178 A1* | 2/2007 | Massimi | B05C 17/035 401/219 |
| 2007/0065481 A1 | 3/2007 | Chudzik et al. | |
| 2007/0101933 A1 | 5/2007 | Chappa | |
| 2007/0116855 A1 | 5/2007 | Fox et al. | |
| 2007/0131165 A1 | 6/2007 | Fox et al. | |
| 2007/0141232 A1 | 6/2007 | Tochterman et al. | |
| 2007/0259100 A1 | 11/2007 | Guerriero et al. | |
| 2007/0259102 A1 | 11/2007 | Mcniven et al. | |
| 2007/0259125 A1 | 11/2007 | O'brien et al. | |
| 2007/0275175 A1 | 11/2007 | Hossainy | |
| 2008/0149025 A1 | 6/2008 | Swenson | |
| 2008/0179781 A1 | 7/2008 | Iwata | |
| 2008/0274266 A1 | 11/2008 | Davis et al. | |
| 2009/0018643 A1 | 1/2009 | Hashi et al. | |

(56) References Cited

U.S. PATENT DOCUMENTS

| | | | |
|---|---|---|---|
| 2009/0054837 A1* | 2/2009 | Von Holst et al. | 604/103.08 |
| 2009/0084311 A1 | 4/2009 | Yoshida et al. | |
| 2009/0090299 A1 | 4/2009 | Menendez et al. | |
| 2009/0176030 A1 | 7/2009 | Carlson et al. | |
| 2009/0269481 A1 | 10/2009 | Chappa et al. | |
| 2009/0317537 A1 | 12/2009 | Andreacchi | |
| 2010/0040766 A1* | 2/2010 | Chappa | B05B 13/0214 427/2.3 |
| 2010/0055294 A1* | 3/2010 | Wang | B05D 1/002 427/2.25 |
| 2010/0070020 A1* | 3/2010 | Hashi et al. | 623/1.15 |
| 2010/0179475 A1* | 7/2010 | Hoffmann et al. | 604/103.02 |
| 2010/0227044 A1 | 9/2010 | Scheer | |
| 2011/0046724 A1* | 2/2011 | Heilmann et al. | 623/1.46 |
| 2011/0104392 A1 | 5/2011 | Carlson et al. | |
| 2011/0151199 A1* | 6/2011 | Nelson | B05D 1/002 428/174 |
| 2011/0238011 A1* | 9/2011 | Scheller et al. | 604/103.02 |
| 2011/0250008 A1* | 10/2011 | Lim | B05B 11/3015 401/188 R |
| 2011/0253170 A1* | 10/2011 | Clark | A46B 13/04 134/6 |
| 2011/0281019 A1* | 11/2011 | Gong et al. | 427/2.1 |
| 2011/0281020 A1 | 11/2011 | Gong et al. | |
| 2011/0311713 A1* | 12/2011 | O'Neill et al. | 427/2.25 |
| 2012/0059317 A1* | 3/2012 | Michiyo et al. | 604/103.07 |
| 2012/0100279 A1 | 4/2012 | Neumann et al. | |
| 2012/0258246 A1 | 10/2012 | Saine et al. | |
| 2012/0315376 A1* | 12/2012 | Nguyen et al. | 427/2.28 |
| 2013/0056020 A1* | 3/2013 | Wilson | B05C 17/00 132/320 |
| 2013/0337147 A1* | 12/2013 | Chappa | A61M 25/1027 427/2.3 |
| 2013/0340192 A1* | 12/2013 | DeCarr | B05C 17/0225 15/230.11 |
| 2014/0153996 A1* | 6/2014 | Ammerman | A45D 34/041 401/219 |
| 2014/0161964 A1 | 6/2014 | Chappa et al. | |
| 2014/0328998 A1 | 11/2014 | Chappa et al. | |
| 2015/0017429 A1* | 1/2015 | Li | C09D 1/00 428/332 |
| 2015/0044376 A1* | 2/2015 | Topf | B05C 9/12 427/355 |
| 2016/0256668 A1 | 9/2016 | Chappa et al. | |
| 2016/0271644 A1* | 9/2016 | Weinmann | B05D 1/26 |
| 2017/0341104 A1* | 11/2017 | Johnston | B05C 17/0217 |
| 2018/0036519 A1 | 2/2018 | Chappa et al. | |
| 2019/0099778 A1* | 4/2019 | Antoniazzi | B05C 17/0212 |
| 2019/0143661 A1* | 5/2019 | Hunt | B05D 1/28 156/60 |
| 2019/0151629 A1 | 5/2019 | Chappa et al. | |

FOREIGN PATENT DOCUMENTS

| | | |
|---|---|---|
| DE | 20200223 | 1/2002 |
| DE | 10053826 | 5/2002 |
| EP | 0096433 | 12/1983 |
| EP | 144873 | 6/1985 |
| EP | 414233 | 2/1991 |
| EP | 0604022 | 6/1994 |
| EP | 0716836 | 6/1996 |
| EP | 0734721 | 10/1996 |
| EP | 0747069 | 12/1996 |
| EP | 0857516 | 2/1998 |
| EP | 0834282 | 4/1998 |
| EP | 0945148 | 9/1999 |
| EP | 1374924 | 1/2004 |
| EP | 1382302 | 1/2004 |
| EP | 2994241 | 3/2016 |
| EP | 3549679 | 10/2019 |
| EP | 2911804 | 7/2020 |
| FR | 1304457 | 8/1962 |
| FR | 2733163 | 10/1996 |
| GB | 757659 A * | 9/1956 ......... B05C 17/0212 |
| GB | 2301296 | 12/1996 |
| JP | 57048354 | 3/1982 |
| JP | 63011547 | 1/1988 |
| JP | H0262550 | 3/1990 |
| JP | H03021367 | 1/1991 |
| JP | 09038546 | 2/1997 |
| JP | 2003039015 | 2/2003 |
| JP | 2005059225 | 3/2005 |
| JP | 06246207 | 9/2006 |
| JP | 08086466 | 4/2008 |
| JP | 2015527092 | 9/2015 |
| JP | 2016504058 | 2/2016 |
| JP | 6445532 | 12/2018 |
| WO | 1993015682 | 8/1993 |
| WO | 00/01322 | 1/2000 |
| WO | 2001021326 | 3/2001 |
| WO | 01/32382 | 5/2001 |
| WO | 2001078626 | 10/2001 |
| WO | 2001094103 | 12/2001 |
| WO | 2002/009786 | 2/2002 |
| WO | 02/20174 | 3/2002 |
| WO | 03/004072 | 1/2003 |
| WO | 2003024615 | 3/2003 |
| WO | 2004028579 | 4/2004 |
| WO | 2004028699 | 4/2004 |
| WO | 2004037126 | 5/2004 |
| WO | 2004037443 | 5/2004 |
| WO | 2004098565 | 11/2004 |
| WO | 2005009297 | 2/2005 |
| WO | 2007100801 | 9/2007 |
| WO | 2008002357 | 1/2008 |
| WO | 2009/13221 | 10/2009 |
| WO | 2010024898 | 3/2010 |
| WO | 2010146096 | 12/2010 |
| WO | 2013181498 | 12/2013 |
| WO | 2014066760 | 5/2014 |
| WO | 2014182833 | 11/2014 |

OTHER PUBLICATIONS

"International Preliminary Report on Patentability," for PCT/US2014/037179 dated Nov. 19, 2015 (9 pages).

"Notice of Allowance," for U.S. Appl. No. 12/109,139 dated Dec. 8, 2015 (20 pages).

"Notice of Allowance," for U.S. Appl. No. 13/906,599 dated Dec. 10, 2015 (6 pages).

"Notice of Allowance," for U.S. Appl. No. 14/063,124 dated Oct. 27, 2015 (10 pages).

"Response Final Office Action," for U.S. Appl. No. 13/906,599, dated Sep. 18, 2015 and filed with the USPTO Nov. 3, 2015 (6 pages).

"Response to Communication Pursuant to Rules 161(1) and 162 EPC," for European Patent Application No. 13792526.9, dated Jul. 7, 2015 and filed with the EPO Jan. 7, 2016 (18 pages).

Braun, Dietrich "Plastics," Concise Encyclopedia of Polymer Science and Engineering, 1990 (pp. 461-464).

"Communication Pursuant to Rules 161 and 162 EPC," for European Patent Application No. 13729853.5, dated Feb. 13, 2015 (2 pages).

"Communication Pursuant to Rules 161(1) and 162 EPC," for European Application No. 13792526.9, dated Jul. 7, 2015 (2 pages).

"Cross-Link," http://en.wikipedia.org/wiki/Cross-link; retrieved Nov. 6, 2009 (4 pages).

"European Examination Report," for European Application No. 06740366.7 dated Oct. 19, 2010 (4 pages).

"European Examination Report," for European Application No. 06740366.7, dated May 5, 2009 (4 pages).

"Final Office Action," for Japanese Application No. 2006-509776, dated Jul. 5, 2011, (7 pages).

"Final Office Action," for U.S. Appl. No. 13/906,599 dated Sep. 18, 2015 (35 pages).

"Final Office Action," for U.S. Appl. No. 11/559,817 dated Apr. 27, 2011 (5 pages).

(56) References Cited

OTHER PUBLICATIONS

"First Office Action," for CA Application No. 2604832, dated Mar. 16, 2012 (4 pages).
Hiemenz, Paul "Polymer Chemistry: The Basic Concepts," CRC Press, 1984 (pp. 9 and 12).
"International Preliminary Report on Patentability," for PCT/US2013/066810, dated May 7, 2015 (12 pages).
"International Preliminary Report on Patentability," from International Application No. PCT/US2004/004486, dated Aug. 19, 2005, (6 pages).
"International Search Report and Written Opinion," for PCT Application No. PCT/US2014/037179 dated Feb. 19, 2015 (15 pages).
"International Search Report and Written Opinion," for PCT/US2006/044218, dated Mar. 22, 2007 (12 pages).
"International Search Report and Written Opinion," for PCT/US2009/041575, dated Jul. 22, 2009 (15 pages).
"International Search Report," for PCT/US2004/004486, dated Jul. 19, 2004, (8 pages).
"Non-Final Office Action," for U.S. Appl. No. 11/102,465, dated Sep. 6, 2011 (18 pages).
"Non-Final Office Action," for U.S. Appl. No. 11/559,817 dated Oct. 13, 2011 (5 pages).
"Non-Final Office Action," for U.S. Appl. No. 14/063,124 dated Apr. 15, 2015 (28 pages).
"Non-Final Office Action," for U.S. Appl. No. 19/906,599 dated Apr. 9, 2015 (19 pages).
"Non-Final Office Action," for U.S. Appl. No. 12/980,920 dated Mar. 15, 2012 (14 pages).
"Notice of Allowance Received," for U.S. Appl. No. 12/980,920, dated Jul. 13, 2012 (5 pages).
"Notice of Allowance," for U.S. Appl. No. 12/109,139 dated Jul. 31, 2015 (7 pages).
"Notice of Allowance," for U.S. Appl. No. 11/102,465, dated Apr. 16, 2012 (18 pages).
"Notice of Allowance," for U.S. Appl. No. 11/559,817 dated Dec. 30, 2011 (7 pages).
"Response to Communication Pursuant to Rules 161 and 162 EPC," for European Patent Application No. 13729853.5, filed with the EPO Aug. 13, 2015 (21 pages).
"Response to European Examination Report," for European Application No. 06740366.7, filed Feb. 22, 2011 (8 pages).
"Response to Non-Final Office Action," for U.S. Appl. No. 13/906,599, dated Apr. 9, 2015 and filed with the USPTO Aug. 10, 2015 (9 pages).
"Response to Non-Final Office Action," for U.S. Appl. No. 14/063,124, dated Apr. 15, 2015 and filed with the USPTO Jul. 15, 2015 (14 pages).
"Ultrasonic Spray Nozzle Systems," Sono-Tek Corporation Brochure, 2005 (16 pages).
Yeo, Yoon "A New Microencapsulation Method Using an Ultrasonic Atomizer Based on Interfacial Solvent Exchange," Journal of Controlled Release 100 (2004) pp. 379-388.
U.S. Appl. No. 10/976,193 "Notice of Allowance dated Mar. 8, 2011", 6 Pgs.
Examiner's Answer, from U.S. Appl. No. 12/109,139, dated Mar. 22, 2013, 12 pages.
"Final Office Action", dated Dec. 28, 2011 in co pending U.S. Appl. No. 12/109,139, "Coating Application System With Shaped Mandrel," (6 Pages)., 6.
"Final Office Action", dated Sep. 4, 2012 in U.S. Appl. No. 12/109,139, "Coating Application System With Shaped Mandrel," (8 pages)., 8.
"International Preliminary Report on Patentability", for PCT Application No. PCT/US2013/043547, dated Dec. 11, 2014 (7 pages).
"International Search Report and Written Opinion", for PCT/US2013/066810, dated Apr. 17, 2014 (18 pages).
"International Search Report and Written Opinion", for PCY/US2013/043547, dated Oct. 1, 2013 (10 pages).
"Invitation to Pay Additional Fees and, Where Applicable, Protest Fee", for PCT/US2013/066810, dated Feb. 7, 2014 (6 pages).
"Invitation to Pay Additional Fees", for PCT Application No. PCT/US2014/037179, dated Oct. 24, 2014 (5 pages).
"Non Final Office Action dated Jul. 14, 2011 in co pending U.S. Appl. No. 12/109,139, "Coating Application System With Shaped Mandrel" (9 pages)", 9 Pgs.
"Non Final Office Action", dated Apr. 4, 2012in co pending U.S. Appl. No. 12/109,139, "Coating Application System With Shaped Mandrel," (8 pages)., 8.
"Office Action dated Jul. 9, 2007 for U.S. Appl. No. 11/539,443".
Office Action dated Oct. 6, 2005 for U.S. Appl. No. 10/976,348.
"Office Action dated Feb. 22, 2006 for U.S. Appl. No. 10/976,348".
"Office Action dated May 17, 2007 for U.S. Appl. No. 10/976,193".
"Office Action dated Jun. 13, 2006 for U.S. Appl. No. 10/976,193".
"Pct International Search Report and Written Opinion from International Application No. PCT/US2005/038628, corresponding to U.S. Appl. No. 10/976,193, dated Mar. 22, 2006, pp. 1-16".
PCT International Search Report and Written Opinion from International Application No. PCT/US2009/041575, corresponding to U.S. Appl. No. 12/109,139, dated Jul. 22, 2009, pp. 1-15.
"Pct Notification Concerning Transmittal of International Preliminary Report on Patentability from International Application No. PCT/US2005/038628, corresponding to U.S. Appl. No. 10/976,193, dated May 10, 2007, pp. 1-10".
"Pto-892 Mailed Jul. 9, 2007 for U.S. Appl. No. 11/539,443".
"Pto-892 Mailed on Oct. 6, 2005 for U.S. Appl. No. 10/976,348".
"Pto-892 Mailed on May 17, 2007 for U.S. Appl. No. 10/976,193".
"Restriction Requirement", for U.S. Appl. No. 14/063,124, dated Oct. 17, 2014 (7 pages).
"Restriction Requirement", for U.S. Appl. No. 13/906,599, dated Dec. 3, 2014 (6 pages).
"Restriction Requirement", dated Apr. 29, 2011 in co pending U.S. Appl. No. 12/109,139, "Coating Application System With Shaped Mandrel," (7 pages)., 7 Pgs.
"Notice of Allowance," for U.S. Appl. No. 15/061,234, dated Dec. 16, 2016 (11 pages).
"Non-Final Office Action," for U.S. Appl. No. 14/272,204 dated Sep. 1, 2016 (50 pages).
"Non-Final Office Action," for U.S. Appl. No. 15/061,234 dated Aug. 26, 2016 (47 pages).
"Response to Communication Pursuant to Rules 161(1) and 162 EPC," for European Patent Application No. 14730319.2, filed with the EPO Jun. 24, 2016 (11 pages).
"Response to Non-Final Office Action," for U.S. Appl. No. 14/272,204, dated Sep. 1, 2016 and filed with the USPTO Nov. 28, 2016 (8 pages).
"Response to Non-Final Office Action," for U.S. Appl. No. 15/061,234, dated Aug. 26, 2016 and filed with the USPTO Nov. 28, 2016 (8 pages).
"Final Office Action," for U.S. Appl. No. 14/272,204 dated Mar. 30, 2017 (12 pages).
"Office Action," for Japanese Patent Application No. 2015-515223 dated Mar. 24, 2017 (10 pages) with English translation.
"Office Action," for Mexican Patent Application No. MX/a/2014/014574 dated Jun. 15, 2017 (1 page), English summary.
"Response to Final Office Action," for U.S. Appl. No. 14/272,204, dated Mar. 30, 2017 and filed with the USPTO Jun. 26, 2017 (7 pages).
"Final Rejection," for Japanese Patent Application No. 2015-515223 dated Nov. 22, 2017 (8 pages) with English translation.
"Response to Communication Pursuant to Rule 164(2)(b) and Article 94(3) EPC," for European Patent Application No. 14730319.2 filed with the EPO Jan. 2, 2018 (19 pages).
"Communication Pursuant to Rule 164(2)(b) and Article 94(3) EPC," for European Patent Application No. 14730319.2 dated Sep. 4, 2017 (12 pages).
"Office Action," for Japanese Patent Application No. 2015-539837 dated Aug. 31, 2017 (11 pages) with English translation.
"Notice of Allowance," for U.S. Appl. No. 15/783,554 dated Aug. 23, 2018 (50 pages).
"Office Action," for Japanese Patent Application No. 2015-539837 dated Jun. 28, 2018 (7 pages) with English translation.

(56) References Cited

OTHER PUBLICATIONS

"Response to Communication Pursuant to Article 94(3) EPC," for European Patent Application No. 13792526.9 filed with the EPO Aug. 17, 2018 (60 pages).
"Communication Pursuant to Article 94(3) EPC," for European Patent Application No. 13729853.5 dated Apr. 30, 2018 (6 pages).
"Communication Pursuant to Article 94(3) EPC," for European Patent Application No. 13792526.9 dated Apr. 19, 2018 (5 pages).
"Non-Final Office Action," for U.S. Appl. No. 15/783,554 dated Mar. 8, 2018 (46 pages).
"Office Action," for Japanese Patent Application No. 2016-513047 dated Mar. 6, 2018 (11 pages) with English translation.
"Response to Non-Final Office Action," for U.S. Appl. No. 15/783,554, dated Mar. 8, 2018 and filed with the USPTO Jun. 14, 2018 (8 pages).
"Communication Pursuant to Article 94(3) EPC," for European Patent Application No. 13792526.9 dated Aug. 6, 2019 (5 pages).
"European Search Report," for European Patent Application No. 19174997.7 dated Sep. 10, 2019 (9 pages).
"Notice of Allowance," for U.S. Appl. No. 16/160,425 dated Aug. 13, 2019 (9 pages).
"Office Action," for Canadian Patent Application No. 2,889,062 dated Sep. 12, 2019 (3 pages).
"Response to Office Action," for Canadian Patent Application No. 2,874,824 filed Oct. 7, 2019 (18 pages).
First Examination Report for Costa Rican Patent Application No. 2014-0589 dated May 19, 2019 (2 pages) No English Translation.
Non-Final Office Action for U.S. Appl. No. 16/160,425 dated Apr. 5, 2019 (50 pages).
Office Action for Canadian Patent Application No. 2,874,824 dated Apr. 11, 2019 (5 pages).
Office Action for Japanese Patent Application No. 2015-515223 dated Feb. 21, 2019 (5 pages) with English Translation.
Pre-Appeal Examination Report for Japanese Patent Application No. 2015-539837 dated Mar. 8, 2019 (2 pages), no translation available.
Response to Communication Pursuant to Article 94(3) EPC for European Patent Application No. 13792526.9 filed Mar. 13, 2019 (6 pages).
Response to Non-Final Rejection dated Apr. 5, 2019 for U.S. Appl. No. 16/160,425, submitted via EFS-Web on Jun. 27, 2019, 7 pages.
"Final Office Action," for Japanese Patent Application No. 2015-539837 dated Oct. 1, 2018 (7 pages) with English Translation.
"Response to Communication Pursuant to Article 94(3) EPC," for European Patent Application No. 13729853.5, filed with the EPO Sep. 6, 2018 (12 pages).
"Communication Pursuant to Article 94(3) EPC," for European Patent Application No. 13792526.9 dated Nov. 29, 2018 (4 pages).
"Office Action," for Canadian Patent Application No. 2,874,824 dated Jan. 9, 2020 (4 pages).
"Response to Communication Pursuant to Article 94(3) EPC," for European Patent Application No. 13792526.9 filed Dec. 3, 2019 (9 pages).
"Office Action Response," for Canadian Patent Application No. 2,889,062 filed Mar. 9, 2020 (18 pages).
"Response to Office Action," for Canadian Patent Application No. 2,874,824 filed May 8, 2020 (15 pages).
"Response to Search Report," for European Patent Application No. 19174997.7 filed Mar. 31, 2020 (30 pages).
"Office Action Response," for Canadian Patent Application No. 2,889,062 filed Sep. 18, 2020 (11 pages).
"Office Action," for Canadian Patent Application No. 2,874,824 dated Aug. 25, 2020 (3 pages).
"Office Action," for Canadian Patent Application No. 2,889,062 dated Jun. 5, 2020 (3 pages).
"Office Action," for Canadian Patent Application No. 2,911,482 dated Jul. 17, 2020 (3 pages).
"Response to Office Action," for Canadian Patent Application No. 2,874,824 filed Nov. 4, 2020 (6 pages).
"Response to Office Action," for Canadian Patent Application No. 2,911,482 filed Oct. 28, 2020 (10 pages).

* cited by examiner

APPARATUS AND METHODS FOR COATING MEDICAL DEVICES

This application claims the benefit of U.S. Provisional Application No. 61/718,358, filed Oct. 25, 2012, the content of which is herein incorporated by reference in its entirety.

FIELD OF THE INVENTION

The present invention relates to apparatus and methods for coating medical devices.

BACKGROUND OF THE INVENTION

Functional improvements to implantable or insertable medical devices can be achieved by coating the surface of the device. For example, a coating formed on the surface of the device can provide improved lubricity, improved biocompatibility, or drug delivery properties to the surface. In turn, this can improve movement of the device in the body, extend the functional life of the device, or treat a medical condition near the site of implantation. However, various challenges exist for the design and use of coating apparatus designed to provide coatings to medical devices.

Traditional coating methods, such as dip coating, are often undesirable as they may result in flawed coatings that could compromise the function of the device or present problems during use. These methods can also result in coating inaccuracies, which can be manifested in variable amounts of the coated material being deposited on the surface of the device. When a drug is included in the coating material, it is often necessary to deliver precise amounts of the agent to the surface of the device to ensure that a subject receiving the coated device receives a proper dose of the agent. It has been difficult to achieve a great degree of accuracy using traditional coating methods and machines.

One type of insertable medical device is a balloon catheter. Balloon catheter constructions are well known in the art and are described in various documents, for example, U.S. Pat. Nos. 4,195,637, 5,041,089, 5,087,246, 5,318,587, 5,382,234, 5,571,089, 5,776,101, 5,807,331, 5,882,336, 6,394,995, 6,517,515, 6,623,504, 6,896,842, and 7,163,523. Balloon catheters generally include four portions, the balloon, catheter shaft, guide wire, and manifold. A balloon catheter generally includes an elongated catheter shaft with an inflatable balloon attached to a distal section of the catheter shaft. At a proximal end of the catheter shaft, there is typically a manifold. At the manifold end, placement of the catheter can be facilitated using a guide wire. Guide wires are small and maneuverable when inserted into an artery. Once the guide wire is moved to the target location, the catheter with balloon portion is then fed over the guide wire until the balloon reaches the target location in the vessel. The balloon is typically inserted into the arterial lumen of a patient and advanced through the lumen in an unexpanded state. The balloon is then inflated when the catheter reaches target site resulting in application of mechanical force sufficient to cause vessel dilation. The balloon is typically inflated using a fluid, which is injected through an inflation port. The manifold can control the fluid introduction within shaft for expansion of the balloon. The mechanics of fluid transfer and introduction within balloons vary according to the specific design of the catheter, and are well known in the art.

SUMMARY OF THE INVENTION

Embodiments of the invention include apparatus and methods for coating medical devices. In an embodiment, the invention includes a coating apparatus including a coating application unit including a fluid applicator; a first rotation mechanism and a second rotation mechanism; and a controller, wherein the controller causes the first rotation mechanism and the second rotation mechanism to rotate a medical device at substantially the same speed, wherein the speed is greater than 500 rotations per minute.

In an embodiment, the invention includes a method of coating a medical device including rotating a medical device with a rotation mechanism at a speed of greater than 500 rotations per minute; contacting the medical device with a fluid applicator; and applying a coating solution to the device with the fluid applicator.

In an embodiment, the invention includes a medical device including a shaft defining a lumen; and an inflatable balloon attached to the shaft; and a coating layer disposed over at least a portion of the shaft; wherein the surface of the shaft comprises high points and low points, wherein the thickness of the coating is substantially the same over both the high points and the low points.

In an embodiment, the invention includes a medical device including a shaft defining a lumen; and an inflatable balloon attached to the shaft, the balloon comprising a plurality of longitudinal pleats; and a coating layer disposed over a portion of the balloon, wherein the coating layer defines apertures that correspond to the longitudinal pleats.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE FIGURES

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Figure 1:
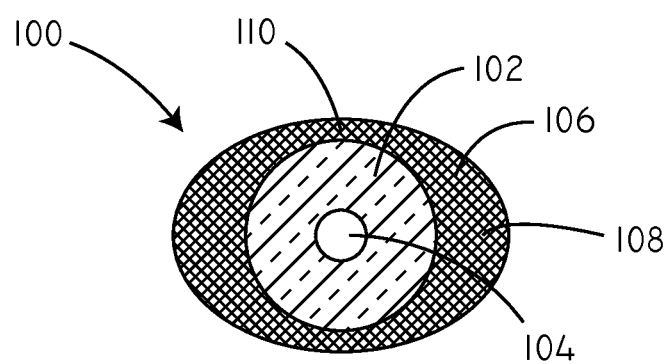
FIG. 1 is a partial cross-sectional view of a device including a shaft with a central lumen.

Standard coating techniques can include dip coating and/or spray coating. Applicants have observed, however, that standard techniques such as dip coating can result in various coating irregularities. By way of example, dip coating can result in coatings that are characterized by a thicker side and a thinner side. Referring to FIG. 1, a cross-sectional view is shown of a device 100 including a shaft 102 with a central lumen 104. The device 100 also includes a coating 106. However, the coating 106 is not disposed evenly around the circumference of the shaft 102. Rather, the coating 106 has a thick side 108 and a thin side 110. This can pose various problems including sub-optimal durability of the coating.

Figure 2A:
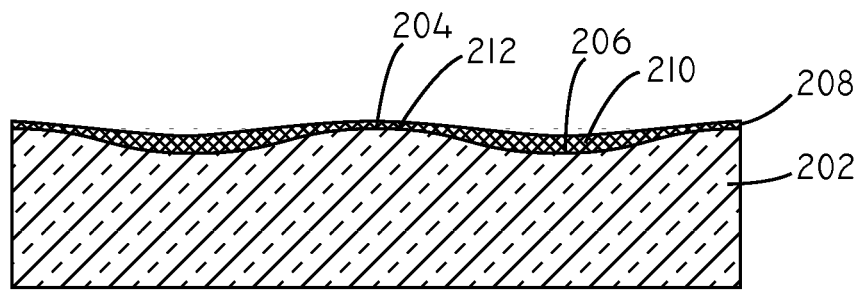
FIG. 2A is a partial cross-sectional view of the substrate of a medical device.

In addition, standard coating techniques can result coating irregularities, particularly where the surface of the object to be coated has some degree of surface topology variation. For example for objects with a surface having a variable topology (high points and low points), there is usually a larger amount of coating material that ends up over the low points and a lesser amount that ends up over the high points. Referring now to FIG. 2A, a partial cross-sectional view is shown of the substrate 202 of a medical device that includes high points 204 and low points 206. A coating 208 is disposed on the substrate 202. The coating includes thicker portions 210 and thinner portions 212. This type of coating pattern can be problematic because the higher points are also subject to a greater degree of friction during use than the low points and so a coating with these types of irregularities can be substantially less durable and more prone to release of particulate matter as the coating breaks down.

Figure 2B:
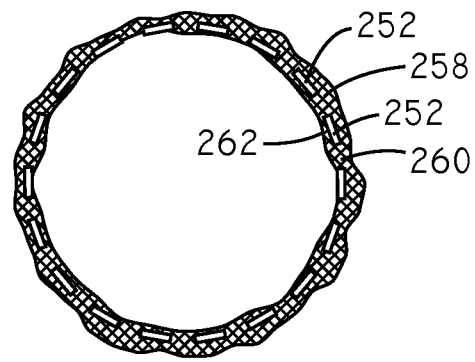
FIG. 2B is a partial cross-sectional view of a medical device.

In the context of medical devices with gaps in between features, standard coating techniques can result in coatings that span the gaps (such as a webbing) and/or flow through to the inner diameter resulting in a coating configuration that is undesirable for some types of applications. Referring now to FIG. 2B, a partial cross-sectional view of a medical device is shown. The medical device includes a plurality of segments 252 separated from one another by gaps 260 (such as slots on the surface of a tube) and surrounding a central lumen. A coating material 258 is disposed on the device. However, the coating material is disposed within the gaps 260 and on the inner diameter surface 262 of the medical device. The coating material between the segments can be susceptible to breaking off and can therefore serve as a source of particulates. In addition, the presence of the coating on the inner diameter can be undesirable if different functional properties are desired between the inner and outer diameter of the medical device.

Embodiments of coating apparatus herein can be used to apply coatings, including coatings with or without active agents, onto medical devices, such as onto the shafts and/or balloons of balloon catheters while addressing various shortcomings of standard coating techniques. Notably, embodiments of coating apparatus herein can be used to coat medical device having uniform coatings that are substantially even around the circumference of the medical device. This has been found to be possible even in the context of coating solutions that are extremely difficult to use in forming even coatings such coating solutions with high viscosities and coatings solutions with low viscosities.

In addition, embodiments of coating apparatus herein can be used to coat medical devices having variable surface topology that result in coatings that are substantially more uniform in terms of the amount of coating applied when comparing high points and low points on the surface. In some embodiments, coating apparatus herein can be used to apply coatings wherein the typical pattern of more coating material over low points is actually reversed such that there is more coating material over high points.

Figure 3:
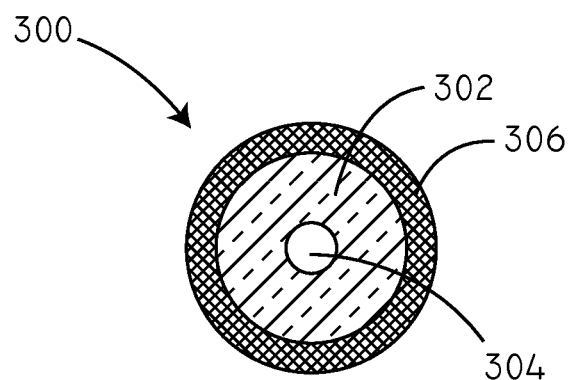
FIG. 3 is a partial cross-sectional view of a device including a shaft with a central lumen in accordance with various embodiments herein.

In various embodiments, coating apparatus herein include rotation mechanisms that spin the medical device to be coated at a relatively high rate. Spinning of the medical device at a high rate results in a substantial centrifugal force being generated that acts to make the thickness of the coating substantially uniform when evaluating the coating thickness around the circumference of a medical device. Referring now to FIG. 3, a cross-sectional view is shown of a device 300 including a shaft 302 with a central lumen 304. The device 300 also includes a coating 306. However, in contrast to the coating 106 shown in FIG. 1, the coating 306 is disposed substantially evenly around the circumference of the shaft 302.

In addition, the substantial centrifugal force counteracts the tendency of coating material to pool in low points which is otherwise true in the context of lower speed spinning or stationary applications. Surprisingly, Applicants have discovered that high RPM spinning can be utilized without the coating solution being thrown off the surface of the medical device after it is applied. In other words, Applicants have discovered that very high rotations per minute can be used in the coating process without the centrifugal force getting so high that the coating material is cast off of the surface of the device being coated.

In some embodiments, the device to be coated is rotated at a speed of between 500 and 2000 rotations per minute (RPM). In some embodiments, the device to be coated can be rotated at a speed of between 600 and 1500 rotations per minute. In some embodiments, the device to be coated can be rotated at a speed of between 700 and 1000 rotations per minute. In some embodiments, the device to be coated can be rotated at a speed greater than 500, 600, 700, 800, 900, 1000, 1100, or 1200 rotations per minute.

Centrifugal force can be calculated according to the following equation (I):

$$Fc = 0.01097 \times M \times r \times n^2 \quad \text{(Equation I)}$$

where
Fc=centrifugal force (N (kg*m/s$^2$))
M=mass (kg)
r=radius (m)
n=RPM

As such, it can be seen that the force varies linearly with radius but non-linearly with RPM. For this reason, it has come as a surprising result that at such high RPM speeds that the coating is able to stay on the surface of the medical device being coated.

The radius of medical devices coated in accordance with embodiments herein can vary. In some embodiments, the radius of the device coated is less than 5 cm, 4 cm, 3 cm, 2 cm, or 1 cm. In some embodiments, the radius of the device coated is between about 0.1 mm and 2 cm. In some embodiments, the radius of the device coated is between about 0.2 mm and 1 cm.

Figure 4:
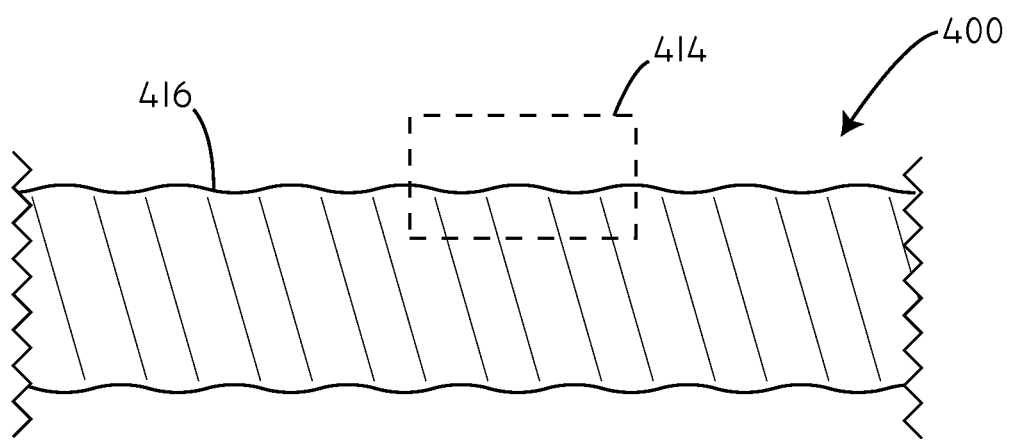
FIG. 4 is a schematic view of a portion of a medical device.
Figure 5A:
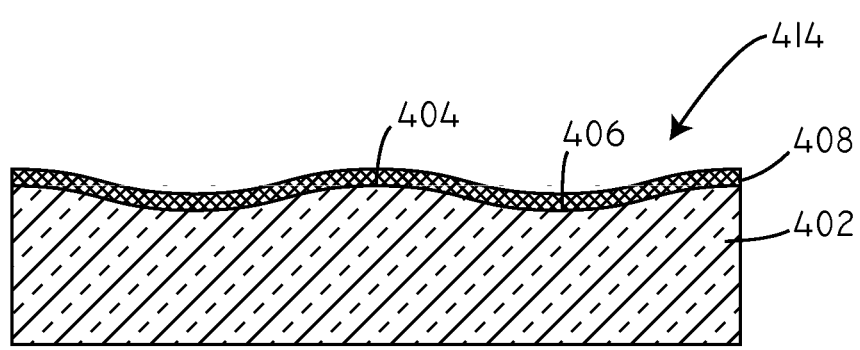
FIG. 5A is a partial cross-sectional view of the substrate of a medical device.

Referring now to FIG. 4, a schematic view is shown of a portion of a medical device 400. The surface 416 of the device 400 has relative high points and low points. Referring now to FIG. 5A, a partial cross-sectional view of a specific segment 414 of the device 400 is shown. The device 400 includes a coating 408 disposed on a substrate 402. The substrate surface includes high points 404 and low points 406. FIG. 5A is distinguished from that shown in FIG. 2 in that the coating 408 is substantially even above both high points 404 and low points 406. While the specific thickness of the coating can vary depending on the end use, it will be appreciated that in various embodiments the thickness can be from about 0.1 microns to about 50 microns. In some embodiments, the thickness can be from 1 to 10 microns.

Exemplary medical devices represented by device 400 can include braided catheters. Braided catheters are typically used in applications that require high torque, burst pressure resistance pushability, steerability and kink resistance. Exemplary uses include EP mapping and ablation catheters, temperature sensing, pressure monitoring, robotic & optical catheters (available Creganna-Tactx Medical, Galway, Ireland).

Figure 5B:
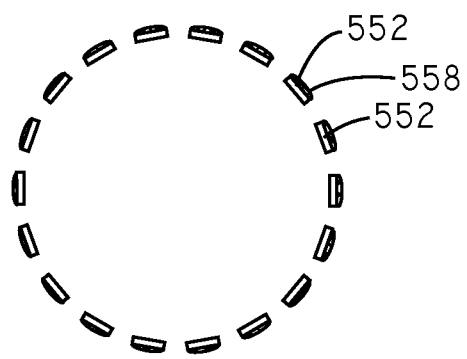
FIG. 5B is a cross-sectional view of a medical device.

Embodiments herein can be used to apply coatings to medical devices with gaps in between features such that the coating does not span the gaps and does not migrate to cover the inner diameter of the medical device. Referring now to FIG. 5B, a partial cross-sectional view of a medical device is shown. The medical device includes a plurality of segments 552 separated from one another by gaps and surrounding a central lumen. A coating material 585 is disposed on the device. However, in contrast to the medical device shown in FIG. 2B, the coating material is not disposed within the gaps and is not on the inner diameter surface 262 of the medical device.

In addition, embodiments herein can be used to apply coatings onto medical devices having porous substrates and/or surfaces and prevent and/or reduce the amount of coating migration from the surface into the porous material. In specific, the centrifugal force provided by the high RPM speeds can serve to at least partially counteract the forces (such as capillary action) that otherwise serve to cause coating materials to migrate into the porous material.

Figure 6:
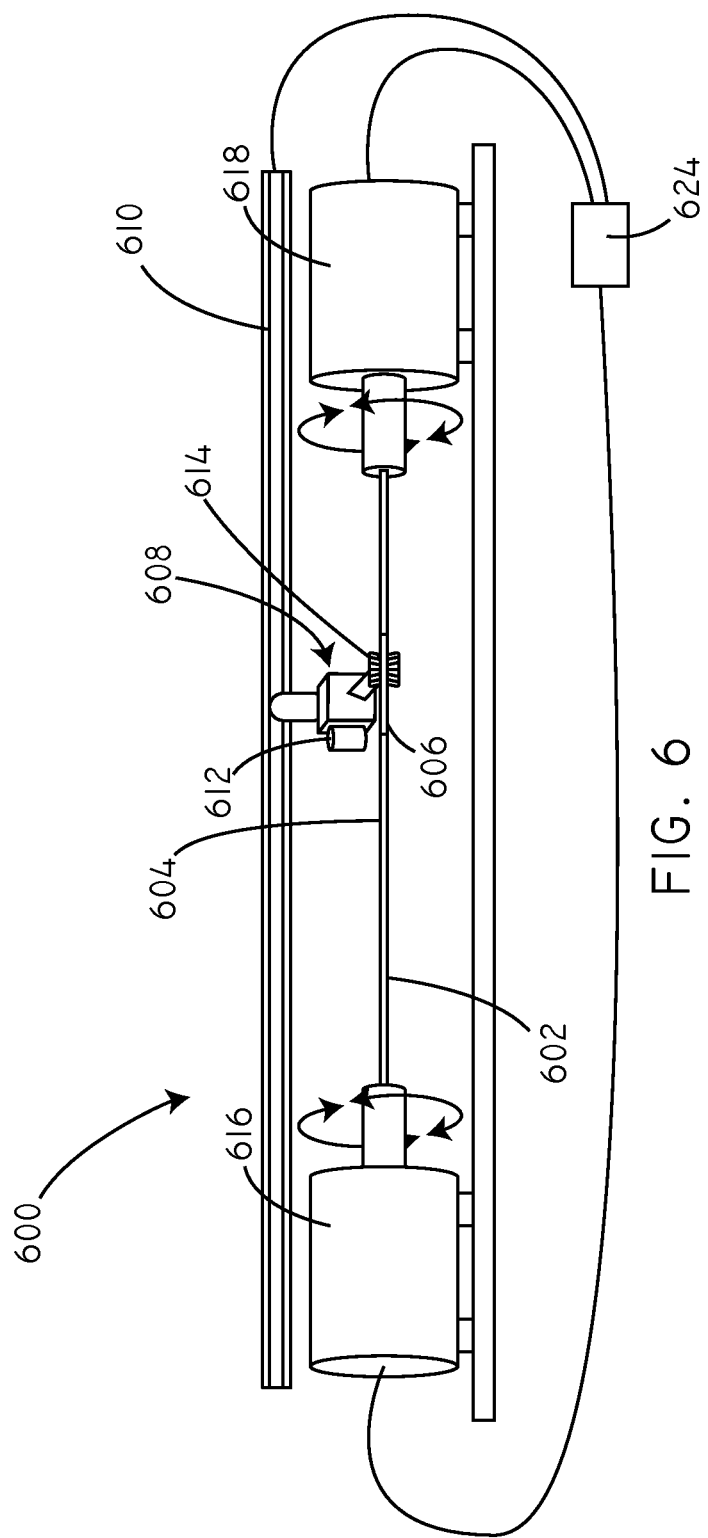
FIG. 6 is a schematic perspective view of a coating apparatus in accordance with various embodiments herein.

Referring now to FIG. 6, a schematic side view is shown of a coating apparatus 600 in accordance with various embodiments herein. The coating apparatus 600 is shown in conjunction with a balloon catheter 602. The balloon catheter 602 can include a catheter shaft 604 and a balloon 606. The balloon 606 can assume a deflated configuration and an inflated configuration. The balloon catheter 602 can include a distal end and a proximal end. The balloon catheter 602 can include a proximal end manifold (not shown). The coating apparatus 600 can include a coating application unit 608. The coating application unit 608 can move along a support rail 610. However, it will be appreciated that in some embodiments, the coating application unit 608 can remain stationary, and other components of the coating apparatus 600 can move.

Coating of the balloon catheter 602 can proceed starting at the proximal end of the and proceeding to the distal end. However, in other embodiments, coating of the balloon catheter 602 can occur starting at the distal end and proceeding to the proximal end. In some embodiments, coating can take place with a single pass of the coating application unit 608 with respect to the balloon catheter 602. However, in other embodiments, multiple passes of the coating application unit 608 with respect to the balloon catheter 602 can be made.

The coating application unit 608 can further include a fluid pump 612. The fluid pump 612 can be, for example, a syringe pump. The fluid pump 612 can be in fluid communication with components of the coating application unit 608 (such as the fluid applicator). The fluid pump 612 can operate to pump a coating solution at a rate sufficient to apply about 0.5 µl to about 10 µl of the coating solution per centimeter of length of the shaft or other portion of the device to be coated. The coating application unit 608 can further include a fluid applicator 614.

In some embodiments the fluid applicator can be a contact fluid applicator (e.g., the fluid applicator makes physical contact with the medical device being coated). While not intending to be bound by theory, it is believed that contact fluid applicators can offer advantages in terms of precise control over the starting and stopping points of segments of coating applied to medical devices, reduced waste (such as material that may otherwise be lost as overspray), and/or control over total amounts of materials deposited onto medical devices (such as active agents and the like). In other embodiments, the fluid applicator is a non-contact fluid applicator. Details of exemplary fluid applicators are provided below.

In contrast to dip coating approaches, embodiments herein can be highly efficient in terms of the use of coating reagents because there is no dead volume or residual volume associated with a container into which a device is dipped. Rather, the amounts of coating reagents used can closely track the amount actually deposited onto medical devices. In some embodiments, greater than 80% of the coating solutions consumed in the process of coating are deposited onto the medical devices being coated. In some embodiments, greater than 90% of the coating solutions consumed in the process of coating are deposited onto the medical devices being coated. In some embodiments, greater than 95% of the coating solutions consumed in the process of coating are deposited onto the medical devices being coated. In some embodiments, greater than 98% of the coating solutions consumed in the process of coating are deposited onto the medical devices being coated. In some embodiments, greater than 99% of the coating solutions consumed in the process of coating are deposited onto the medical devices being coated.

In some embodiments, the rate at which a coating solution is applied to the surface of the medical device can be dynamically changed based on the relative size of the portion being coated. By way of example, it will be appreciated that in order to provide a coating a given thickness, the relative amount of coating solution needed will change based on the diameter of the device to be coated with larger diameters requiring greater amounts of coating solution. As such, in various embodiments, the rate at which coating solution is applied to the surface of a medical device can be dynamically changed according to the diameter (or other size measure) of the portion currently being coated. In some embodiments, a contact fluid applicator can be used to sense the size of the medical device being coated and this information can be used by a controller to dynamically calculate and appropriate rate of application of coating solution (or pumping rate).

The coating apparatus 600 can further include a first rotation mechanism 616 (or rotating balloon catheter fixture) and a second rotation mechanism 618 (or rotating balloon catheter fixture). The rotation mechanisms 616, 618 can be directly or indirectly coupled to the balloon catheter in order to rotate the balloon catheter 602 around its lengthwise (major) axis (about the central lumen of the catheter). The rotation mechanisms can spin at a high rate in order to generate a substantial centrifugal force pulling coating material in an outward direction away from the central lumen of the catheter. In some embodiments, the balloon catheter can be rotated at a speed of between 500 and 2000 rotations per minute. In some embodiments, the balloon catheter can be rotated at a speed of between 600 and 1500 rotations per minute. In some embodiments, the balloon catheter can be rotated at a speed of between 700 and 1000 rotations per minute. In some embodiments, the balloon catheter can be rotated at a speed greater than 500, 600, 700, 800, 900, or 1000 rotations per minute.

It will be appreciated that in many embodiments the medical device to be coated is relatively flexible such that if one end is rotated and the other is not the device will twist. Excessive twisting can be detrimental to the quality of the coating disposed thereon. As such, in some embodiments the rotation mechanisms are configured to reduce or eliminate twisting of the medical device. In some embodiments, the rotation mechanisms can include electric motors. In some embodiments, the motors are in electrical communication in order to ensure that they are turning at the same speed, which can help to prevent twisting of the medical device being coated. In some embodiments, only a single electric motor is used and the motive force therefrom is transmitted to both rotation mechanisms. For example, motive force from an electric motor can be transmitted to the rotation mechanisms through components such as gears, drive shafts, belts, and the like.

In some embodiments one or both of the rotation mechanisms can include clutch mechanisms that can be selectively activated. For example, the clutch mechanism can be used to selectively engage or disengage the source of rotational power in one or both of the rotation mechanisms from the medical device to be rotated. In various embodiments such an arrangement can be used to begin turning electric motors at a synchronized speed before engaging the clutch to begin rotating the medical device.

In some embodiments, a guide wire, passing through the central lumen of the catheter, can extend from the distal tip of the catheter and be inserted into a distal tip support ring or guide. In this manner, the guide wire can be used to support the distal tip of the balloon catheter to be coated while allowing the balloon catheter to rotate freely. In other embodiments, a connection between the exterior of the catheter and a rotation mechanism can be made directly.

The coating apparatus 600 can further include, in some embodiments, an axial motion mechanism which can be configured to move the balloon catheter in the direction of its lengthwise major axis. In some embodiments, axial motion can be substantially horizontal. In other embodiments, axial motion can be substantially vertical. In some embodiments, axial motion can be somewhere in between horizontal and vertical, depending on the orientation of the lengthwise axis of the balloon catheter. In some embodiments, the axial motion mechanism can be a linear actuator. In some embodiments, the axial motion mechanism can include an electric motor.

The coating apparatus 600 can further include a controller 624 that can serve to control operation of the coating apparatus 600 including, specifically, coating application unit 608, fluid pump 612, rotation mechanism 616, rotation mechanism 618, and/or other components of the system. The controller 624 can include various components such as a processor, memory (such as RAM), input and output channels, power supply, and the like. In some embodiments, the controller 624 can specifically include a motor controller.

It will be appreciated that in various embodiments the coating application unit can move, in other embodiments the rotation mechanisms along with the medical device being coated can move, and in still other embodiments other both the coating application unit and the other components such as the rotation mechanisms can all move with respect to one another.

In various embodiments the coating solution being applied can include a component that is activated such as by actinic radiation. In such embodiments, the coating apparatus can further include an actinic radiation source, such as a UV light source.

Figure 7:
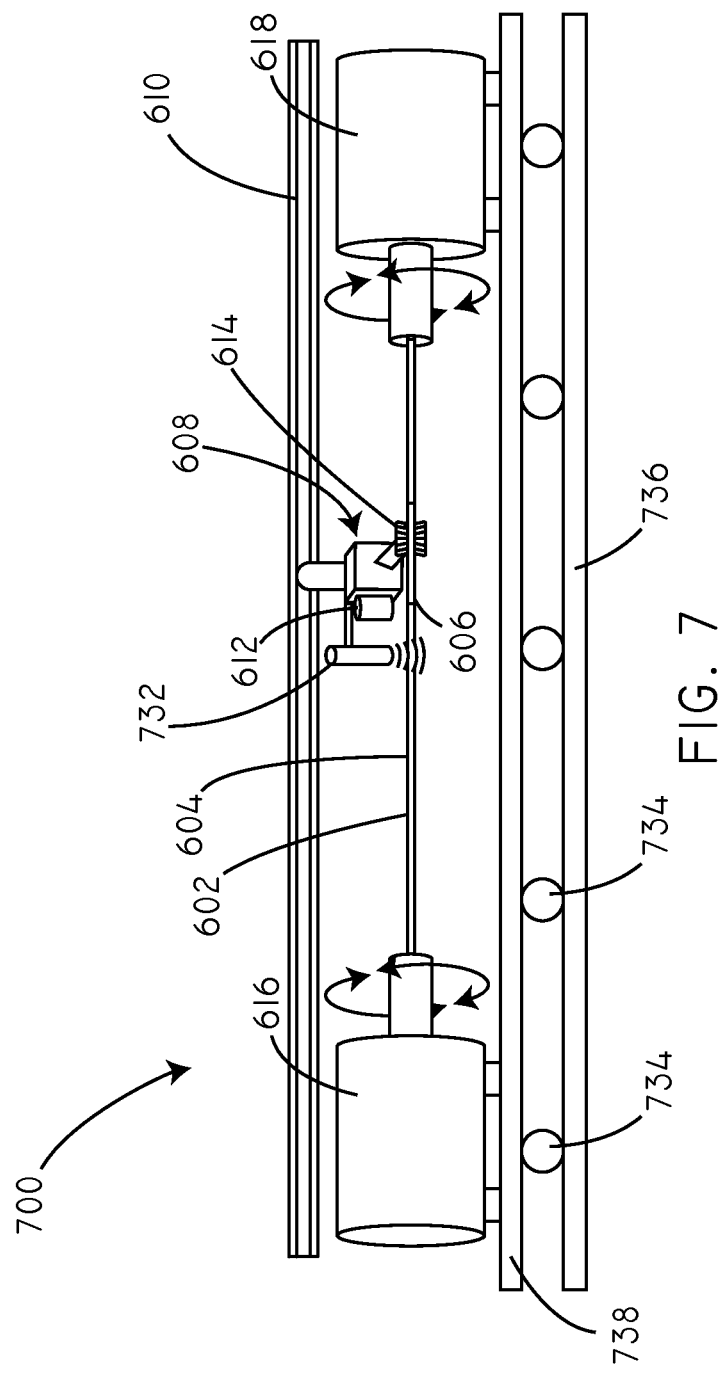
FIG. 7 is a schematic perspective view of a coating apparatus in accordance with various embodiments herein.

Referring now to FIG. 7, a schematic side view is shown of a coating apparatus 700 in accordance with various embodiments herein. In this embodiment, the coating apparatus 700 includes an actinic radiation source 732. The actinic radiation source 732 can include a UV light source. The coating apparatus 700 can further include a mechanism (s) to allow the rotation mechanisms 616, 618 to move in the direction of the lengthwise axis of the medical device. By way of example, the coating apparatus 700 can include rollers 734 that allow the rotation mechanisms and the platform 738 to which they are mounted to move with respect to an underlying support 736.

Fluid Applicator

Figure 8:
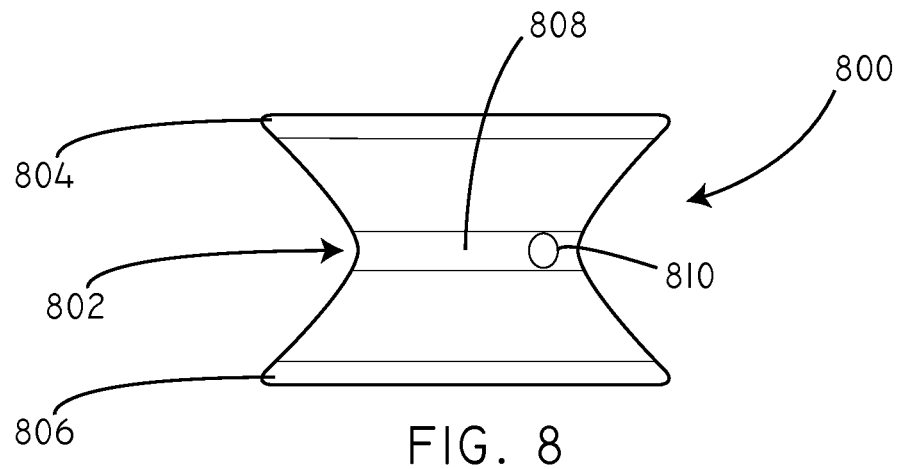
FIG. 8 is a front elevational view of a fluid applicator in accordance with various embodiments herein.
Figure 9:
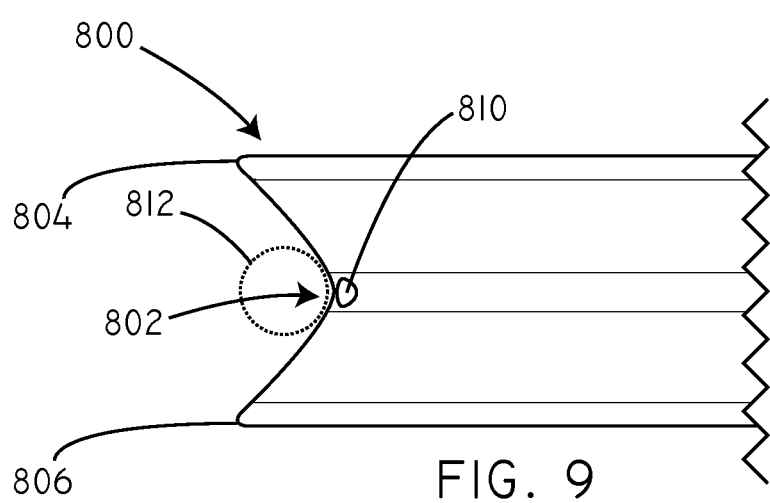
FIG. 9 is a side elevational view of the fluid applicator of FIG. 8 in accordance with various embodiments herein.
Figure 10:
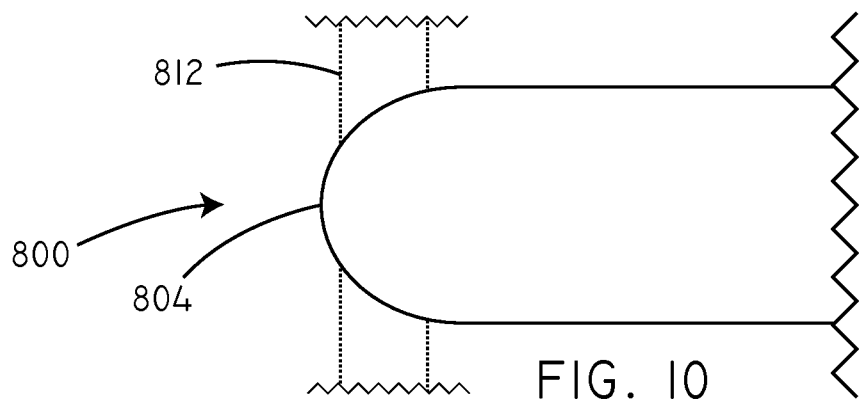
FIG. 10 is a top plan view of the fluid applicator of FIG. 8 in accordance with various embodiments herein.

It will be appreciated that the fluid applicator can take on various forms in accordance with embodiments herein. In some embodiments, the fluid applicator can be configured to maintain contact with the medical device being coated despite the high rate of rotation. Referring now to FIG. 8, a front elevational view of a fluid applicator 800 is shown in accordance with various embodiments herein. The fluid applicator 800 includes a fluid orifice 810. The fluid orifice 810 can be positioned in various areas. In some embodiments, the fluid orifice 810 is positioned at a point away from a lateral center point 808 of the fluid applicator 800. The fluid applicator 800 can include a top 804, a bottom 806, and a middle 802 that is undercut with respect to the top 804 and the bottom 806. As such, the top 804, bottom 806, and middle 802 can form a U-channel. The medical device to be coated can fit within (in whole or in part) with the U-channel. The U-channel can wrap around the entire front of the fluid applicator 800 in some embodiments. Referring now to FIG. 9, a side elevational view of the fluid applicator 800 is shown in accordance with various embodiments herein. In this view, it can be seen that the U-channel can wrap around onto the side of the fluid applicator 800. As such, the U-channel can extend along a radius of curvature away from the lateral center point 808. In this view, the perimeter of an exemplary medical device 812 is superimposed into the figure in order to illustrate how the medical device 812 that interface with the fluid applicator 800. Referring now to FIG. 10, a top plan view of the fluid applicator 800 is shown in accordance with various embodiments herein. While not intending to be bound by theory, applicants have found that the type of fluid applicator shown FIGS. 8-10 can be particularly useful in the context of coating processes wherein multiple passes of the coating application unit with respect to the medical device are made.

Figure 11:
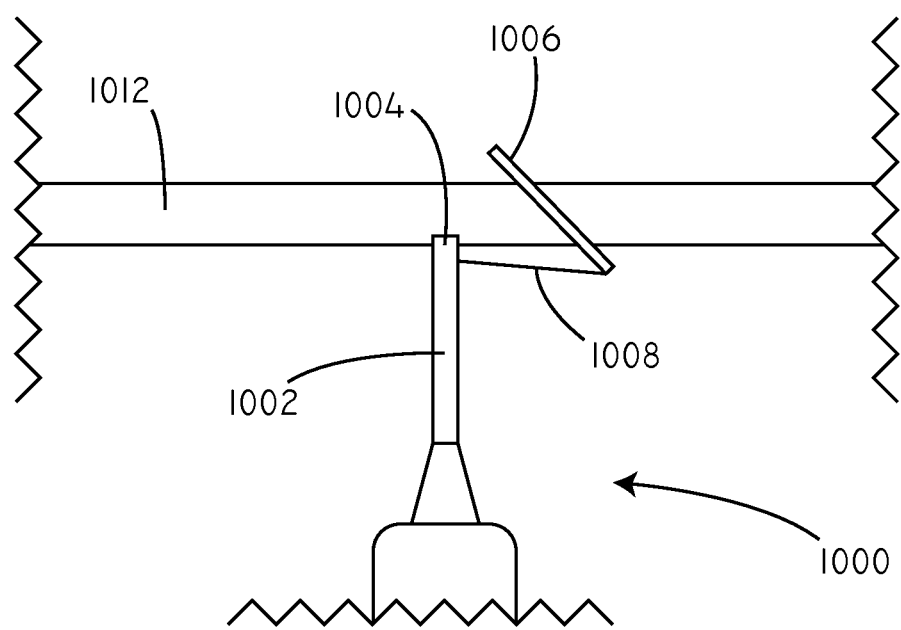
FIG. 11 is a schematic view of a fluid applicator in accordance with various embodiments herein.

Referring now to FIG. 11, a schematic view of a fluid applicator 1000 is shown in accordance with another embodiment of the invention. The fluid applicator 1000 includes a fluid conduit 1002 at the end of which is a fluid orifice 1004. The fluid applicator 1000 also can include a connector 1008 and a contact bar 1006. The contact bar 1006 is oriented such that it contacts the medical device to be coated 1012 when the fluid applicator is oriented in a position to apply the coating solution to the medical device 1012. The connector can exhibit a spring force upon movement of the contact bar 1006 relative to the fluid conduit 1002. While the connector 1008 is shown attached to the fluid conduit 1002 in this embodiment, it will be appreciated that the connector 1008 can also be attached to other components of the fluid applicator 1000 and/or the coating apparatus.

Medical Devices

Figure 12:
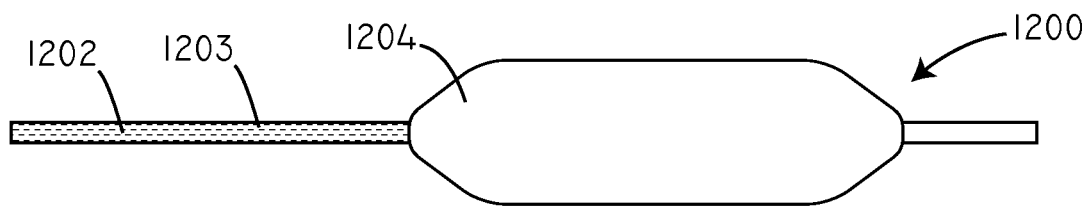
FIG. 12 is a partial view of a medical device with a coating in accordance with various embodiments herein.

The coating apparatus of embodiments herein allows the precise application of coating materials onto medical devices with an extraordinary degree of control regarding where the coating stops and starts along the length of the medical device and the amount of coating applied. In addition, the high rotations per minute at which embodiments herein operate allows for certain types of coatings to be applied that are otherwise impossible. Referring now to FIG. 12, an embodiment of a medical device 1200 is shown (in an inflated configuration) that is included within the scope herein. The medical device 1200 includes a shaft 1202 and a balloon 1204. A coating material is 1203 is disposed on the shaft 1202 on one side of the balloon 1204, but not on the balloon 1204 itself and not on the other side of the balloon.

Figure 13:
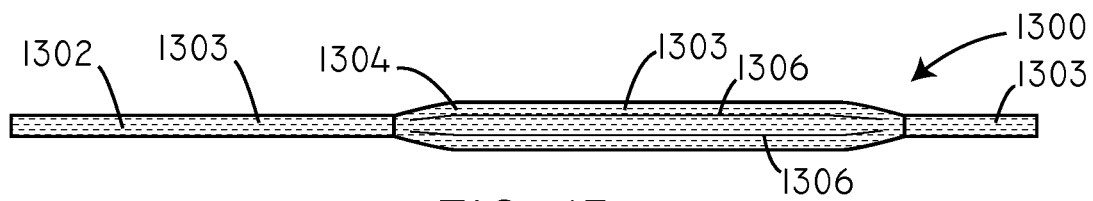
FIG. 13 is a partial view of a medical device with a coating in accordance with various embodiments herein.
Figure 14:
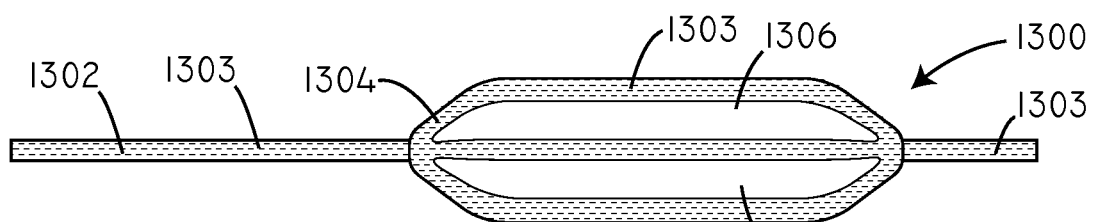
FIG. 14 is a partial view of a medical device with a coating in accordance with various embodiments herein.
Figure 15:
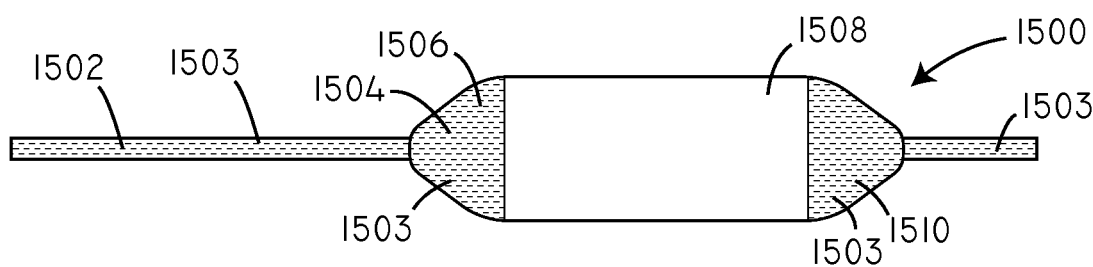
FIG. 15 is a partial view of a medical device with a coating in accordance with various embodiments herein.

Referring now to FIG. 13, an embodiment of a medical device 1300 is shown (in a deflated configuration) that is included within the scope herein. The medical device 1300 includes a shaft 1302 and a balloon 1304. A coating material is 1303 is disposed on the shaft 1302 and on the balloon 1304. The balloon 1304 includes longitudinal pleats or folds 1306 when it is in a deflated configuration. FIG. 14 shows the same medical device 1300 in an inflated configuration. In this view it can be seen that the coating covers most of the balloon 1304 but does not cover the balloon 1304 in the areas of the longitudinal pleats or folds 1306. As such, the coating layer defines apertures in the areas of the longitudinal pleats.

In some embodiments, only a small amount of coating material is drawn into the area of the pleats. By way of example, the amount of coating material in the area of the pleats (as measured when the balloon is expanded) is less than 10% for a given amount of surface area than in the fully coated portion of the balloon (such as in the area outside of the longitudinal pleats). In some embodiments, the amount of coating material in the area of the pleats is less than 5% for a given amount of surface area than in the fully coated portion of the balloon. In some embodiments, the amount of coating material in the area of the pleats is less than 2% for a given amount of surface area than in the fully coated portion of the balloon. In some embodiments, the amount of coating material in the area of the pleats is less than 1% for a given amount of surface area than in the fully coated portion of the balloon.

Referring now to FIG. 14, an embodiment of a medical device 1500 is shown (in an inflated configuration) that is included within the scope herein. The medical device 1500 includes a shaft 1502 and a balloon 1504. A coating material 1503 is disposed on the shaft 1502 on one side of the balloon 1504, in a first area 1506 on one end of the balloon 1504, in a second area 1510 on the other end of the balloon 1504, and on the shaft 1502 on the other side of the balloon 1504. The coating material 1503 is not disposed in a middle segment 1508 of the balloon.

While examples have been provided in the context of balloon catheters, it will be appreciated that many different types of medical devices can be coated in accordance with embodiments herein. By way of example, medical devices can include, but are not limited to catheters, guide wires, leads, stents, grafts, conduits, or any other type of rotatable medical device or medical device component. In various embodiments, medical devices herein include devices with tubular portions. In various embodiments, medical device herein include rotatable medical devices.

Other medical devices that can be coated using embodiments described herein include medical devices with embolic protection filters on the distal end of the catheter. It can be desirable to have the embolic protection filter either coated with a different coating than the catheter guide wire (e.g. heparin), or the embolic protection filter can remain free of coating. This allows for the device to be economically coated for specific purposes, whereas dip coating, for example, could not accomplish this purpose without tedious masking of the parts that are to remain uncoated.

Yet other medical devices that benefit from the coating methods and apparatus described herein are medical devices that have electrodes or sensors as an integral aspect of the medical device (e.g. glucose sensors, pacemaker leads, etc.). Coatings can impede or change the sensitivity of the sensors or electrodes to yield spurious, inaccurate measurements. Coatings conducted in accordance with the embodiments described herein can produce discontinuous coatings at the site of the sensor or electrode on the medical device, thus avoiding the problem of having the coating interfere with the output measurement of the electrode or sensor.

Some embodiments of the coatings applying the present disclosure can be used to apply discontinuous coatings to a catheter guide wire. For example, the distal tip of a guide wire may beneficially be left uncoated so that the physician can maintain a "feel" when placing the catheter into a human. This "feel" can be changed or completely eliminated if the distal tip of the catheter is coated, for example, with a lubricious material.

Other medical devices that can benefit from coating embodiments described herein include medical devices with small apertures or holes (e.g. atherectomy devices for removal of atherosclerotic tissue such as SILVERHAWK™ plaque excision system, available from Foxhollow Technologies). In order for these types of medical devices to function properly the small apertures or holes must remain open. In some instances, the use of dip coating on these devices can plug small apertures, thus decreasing the efficiency or rendering useless the function of the medical device. Discontinuous coatings achieved using the embodiments described herein can minimize or eliminate aperture plugging with coating materials.

Coating Solutions

It will be appreciated that coating solutions applied onto balloons can include various components including, but not limited to, one or more active agents, carrier agents, solvents (aqueous and/or non-aqueous), polymers (including degradable or non-degradable polymers), monomers, macromere, excipients, photoreactive compounds, linking agents, and the like. The relative amounts of the components of the coating solution will depend on various factors.

The coating solutions can be formulated so as to provide various functional properties to the medical device to which they are applied. By way of example, the coating solutions can be formulated so as to provide lubricious properties; anti-infective properties, therapeutic properties, durability and the like.

Viscosities of coating solutions used in conjunction with embodiments herein can vary. In some embodiments, the coating solution is relatively viscous. By way of example, in some embodiments, the coating solution can have a viscosity of 50, 100, 300, 500, 1000, 5000, or 10,000 centipoise or greater. In some embodiments, the coating solution can have a viscosity of between about 50 and 5000 centipoise.

In other embodiments, the coating solution has relatively low viscosity. By way of example, in some embodiments, the coating solution can have viscosity of less than about 50, 40, 30, 20, or 10 centipoise. In some embodiments, the coating solution can have a viscosity of between about 1 and 50 centipoise.

In some embodiments, the coating solution has a solids content that is relatively low. By way of example, in some embodiments, coating solutions used in conjunction with embodiments herein has a solids content of less than about 10 mg/ml. In some embodiments, coating solutions used in conjunction with embodiments herein has a solids content of less than about 5 mg/ml. In some embodiments, coating solutions used in conjunction with embodiments herein has a solids content of less than about 2 mg/ml.

Methods

Embodiments herein include methods of applying coatings onto medical devices. In an embodiment, the method can include rotating a medical device with a rotation mechanism. In some embodiments the medical device can be a balloon catheter a shaft and a balloon. In some embodiments, the medical device can be rotated at a speed of between 500 and 2000 rotations per minute. In some embodiments, the medical device can be rotated at a speed of between 600 and 1500 rotations per minute. In some embodiments, the medical device can be rotated at a speed of between 700 and 1000 rotations per minute. In some embodiments, the medical device can be rotated at a speed greater than 500, 600, 700, 800, 900, or 1000 rotations per minute.

In some embodiments, the rotation mechanism can include a first rotation mechanism and a second rotation mechanism. In some embodiments, the methods can include securing the medical device with the first rotation mechanism and the second rotation mechanism.

In some embodiments, the method can include moving the fluid applicator relative to the lengthwise axis of the medical device. In some embodiments, the method can include moving the medical device along its lengthwise axis relative to the fluid applicator. In still other embodiments, both the fluid applicator and the medical device can be moved.

In some embodiments, applying a coating solution onto the surface of the balloon with a fluid applicator is accomplished through direct contact between the surface of the device with the fluid applicator. In other embodiments, there is no direct contact between the surface of the device and the fluid applicator.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

The invention claimed is:

1. A coating apparatus comprising:
   a rotationally stationary coating application unit comprising;
   a contact fluid applicator comprising a U-shaped curved unitary surface having a top, a bottom, and a middle, wherein the middle is undercut with respect to the top and the bottom to form a U-channel, wherein the U-channel extends along a radius of curvature away from a lateral center point at a front of the contact fluid applicator and wraps around along each of two parallel straight sides of the contact fluid applicator;
   wherein the U-channel is open on the two sides; and
   wherein the contact fluid applicator is configured to contact a medical device within the U-channel, wherein the U-channel is further configured to wrap at least part way around a lengthwise axis of the medical device in a radial direction;
   a first rotation mechanism and a second rotation mechanism; and
   a controller, wherein the controller causes the first rotation mechanism and the second rotation mechanism to rotate the medical device within the U-channel at substantially the same speed, wherein the speed is greater than 500 rotations per minute.

2. The coating apparatus of claim 1, wherein the first rotation mechanism and second rotation mechanism move in the direction of the lengthwise axis of the medical device.

3. The coating apparatus of claim 1, further comprising an electric motor providing power to at least one of the first and second rotation mechanisms.

4. The coating apparatus of claim 1, further comprising a fluid pump in fluid communication with the fluid applicator.

5. The coating apparatus of claim 1, comprising a fluid orifice defined by the fluid applicator at point away from a lateral center point of the fluid applicator.

6. The coating apparatus of claim 1, the contact fluid applicator comprising a fluid conduit, a contact bar, and a connector, the connector connecting the contact bar to the contact fluid applicator, wherein the connector exhibits a spring force upon movement of the contact bar relative to the fluid conduit.

7. The coating apparatus of claim 1, wherein the medical device is a balloon catheter.

8. A method of coating comprising:
rotating a medical device with a rotation mechanism at a speed of greater than 500 rotations per minute;
contacting the medical device with a contact fluid applicator comprising a U-shaped curved unitary surface having a top, a bottom, and a middle, wherein the middle is undercut with respect to the top and the bottom to form a U-channel, wherein the U-channel extends along a radius of curvature away from a lateral center point at a front of the contact fluid applicator and wraps around along each of two parallel straight sides of the contact fluid applicator;
wherein the U-channel is open along the two sides; and
wherein the medical device is directly contacted by the U-channel, the medical device comprising a lengthwise axis, the medical device oriented such that the U-channel wraps at least part way around a lengthwise axis of the medical device in a radial direction; and
applying a coating solution to the device with the contact fluid applicator.

9. The method of claim 8, the rotation mechanism comprising a first rotation mechanism and a second rotation mechanism.

10. The method of claim 9, further comprising securing the medical device with the first rotation mechanism and the second rotation mechanism.

11. The method of claim 8, further comprising moving the fluid applicator along the lengthwise axis of the medical device.

12. The method of claim 8, wherein applying the coating solution onto the surface of a balloon with a fluid applicator is accomplished through direct contact between the surface of the device with the fluid applicator.

13. The method of claim 8, wherein the coating solution has a viscosity of between 1 and 50 centipoise.

14. The method of claim 8, wherein the coating solution has a viscosity of between 50 and 5000 centipoise.

15. A coating apparatus comprising:
a rotationally stationary coating application unit comprising;
a contact fluid applicator comprising a U-shaped curved unitary surface having a top, a bottom, and a middle, wherein the middle is undercut with respect to the top and the bottom to form a U-channel, wherein the U-channel extends along a radius of curvature away from a lateral center point at a front of the contact fluid applicator and wraps around along each of two parallel straight sides of the contact fluid applicator;
wherein the U-channel is open on the two sides; and
wherein the contact fluid applicator is configured to contact a medical device within the U-channel, wherein the U-channel extends along a radius of curvature around an axis that is perpendicular to a lengthwise axis of the medical device;
a first rotation mechanism and a second rotation mechanism; and
a controller, wherein the controller causes the first rotation mechanism and the second rotation mechanism to rotate the medical device within the U-channel at substantially the same speed, wherein the speed is greater than 500 rotations per minute.

16. The coating apparatus of claim 15, wherein the U-channel is curved around a curved axis.

17. The coating apparatus of claim 1, wherein the U-channel extends around an axis that is perpendicular to a lengthwise axis of the medical device such that the U-channel is curved.

* * * * *